United States Patent
Katsuyama

(10) Patent No.: US 10,299,758 B2
(45) Date of Patent: May 28, 2019

(54) ULTRASOUND DIAGNOSTIC DEVICE, ULTRASOUND DIAGNOSTIC METHOD, AND ULTRASOUND DIAGNOSTIC PROGRAM

(71) Applicant: FUJIFILM CORPORATION, Minato-ku, Tokyo (JP)

(72) Inventor: Kimito Katsuyama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 510 days.

(21) Appl. No.: 14/981,872

(22) Filed: Dec. 28, 2015

(65) Prior Publication Data

US 2016/0113624 A1    Apr. 28, 2016

Related U.S. Application Data

(63) Continuation of application No. PCT/JP2014/061198, filed on Apr. 21, 2014.

(30) Foreign Application Priority Data

Jul. 30, 2013    (JP) .................................. 2013-157656

(51) Int. Cl.
*A61B 8/00* (2006.01)
*A61B 8/08* (2006.01)
(Continued)

(52) U.S. Cl.
CPC .......... *A61B 8/4483* (2013.01); *A61B 8/0841* (2013.01); *A61B 8/5207* (2013.01);
(Continued)

(58) Field of Classification Search
None
See application file for complete search history.

(56) References Cited

U.S. PATENT DOCUMENTS

2010/0056917 A1* 3/2010 Karasawa ............ A61B 8/0833
600/443

FOREIGN PATENT DOCUMENTS

JP    S58-44372 A    3/1983
JP    S5844372    *    3/1983
(Continued)

OTHER PUBLICATIONS

Powers et al., "Medical ultrasound systems". Interface Focus (2011) 1, 477-489.*
(Continued)

*Primary Examiner* — Katherine Fernandez
*Assistant Examiner* — Yi-Shan Yang
(74) *Attorney, Agent, or Firm* — SOLARIS Intellectual Property Group, PLLC

(57) ABSTRACT

An ultrasound diagnostic device includes: a probe including plural elements that generate and transmit ultrasound waves and receive ultrasound waves reflected from an inspection target; a transmission unit that transmits ultrasound waves from the plural elements so as to transmit an ultrasound beam by forming a transmission focus in a first direction set in advance; and a second reception focusing unit that performs reception focusing for each reception signal received by each element of the probe according to reflection on a path in a second direction other than the first direction, among transmission wave paths of the ultrasound beam transmitted into the inspection target by the transmission unit.

24 Claims, 16 Drawing Sheets

(51) Int. Cl.
*G01S 15/89* (2006.01)
*G01S 7/52* (2006.01)

(52) U.S. Cl.
CPC ...... *G01S 7/52028* (2013.01); *G01S 15/8915* (2013.01); *G01S 15/8995* (2013.01)

(56) References Cited

FOREIGN PATENT DOCUMENTS

| | | | |
|---|---|---|---|
| JP | 2006-346176 A | | 12/2006 |
| JP | 2006346176 A | * | 12/2006 |
| JP | 2010-51379 A | | 3/2010 |
| JP | 2012-213606 A | | 11/2012 |
| JP | 2012-245092 A | | 12/2012 |
| JP | 2012245092 A | * | 12/2012 |

OTHER PUBLICATIONS

Yang et al., Chapter 8: "Spherical Waves and Cylindrical Waves" in Foundation of Stress Waves, 2007.*
International Search Report issued in International Application No. PCT/JP2014/061198 dated May 20, 2014.
Written Opinion of the ISA issued in International Application No. PCT/JP2014/061198 dated May 20, 2014.
Japanese Office Action dated Oct. 18, 2016 in corresponding Japanese Patent Application No. 2013-157656 and a Partial English Translation thereof.
English language translation of the following: Office action dated May 27, 2017 from the SIPO in a Chinese patent application No. 201480040259.7 corresponding to the instant patent application. This office action translation is submitted now in order to supplement the understanding of the cited reference which is being disclosed in the instant Information Disclosure Statement.

* cited by examiner

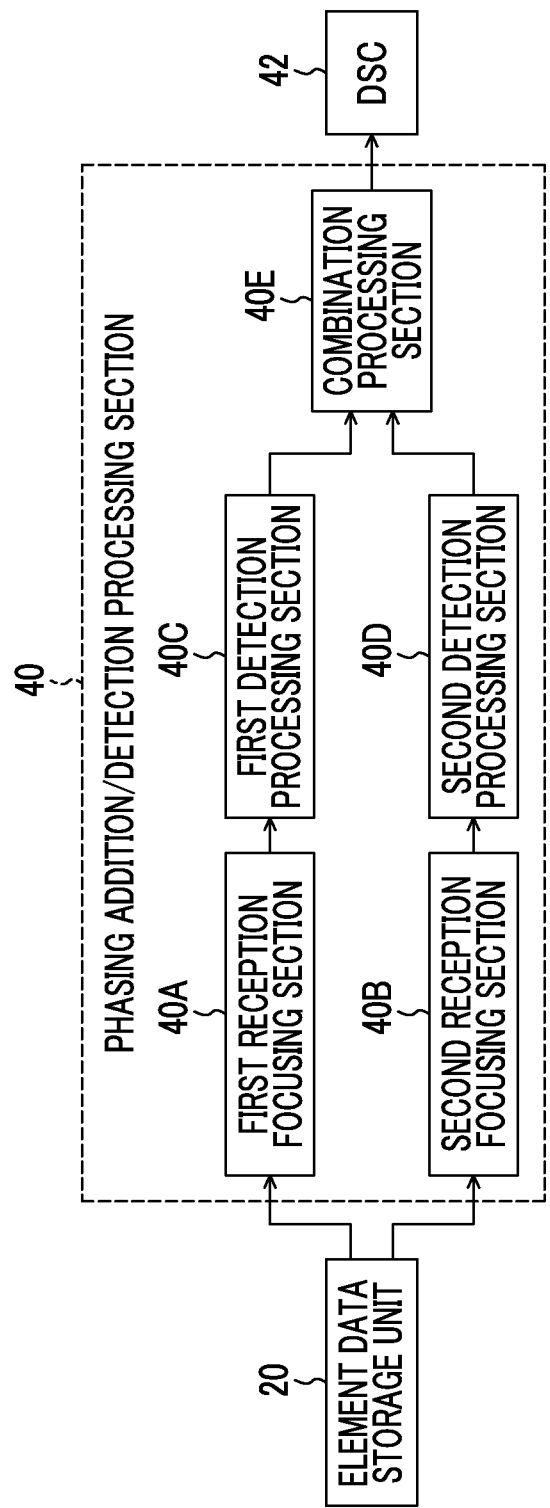

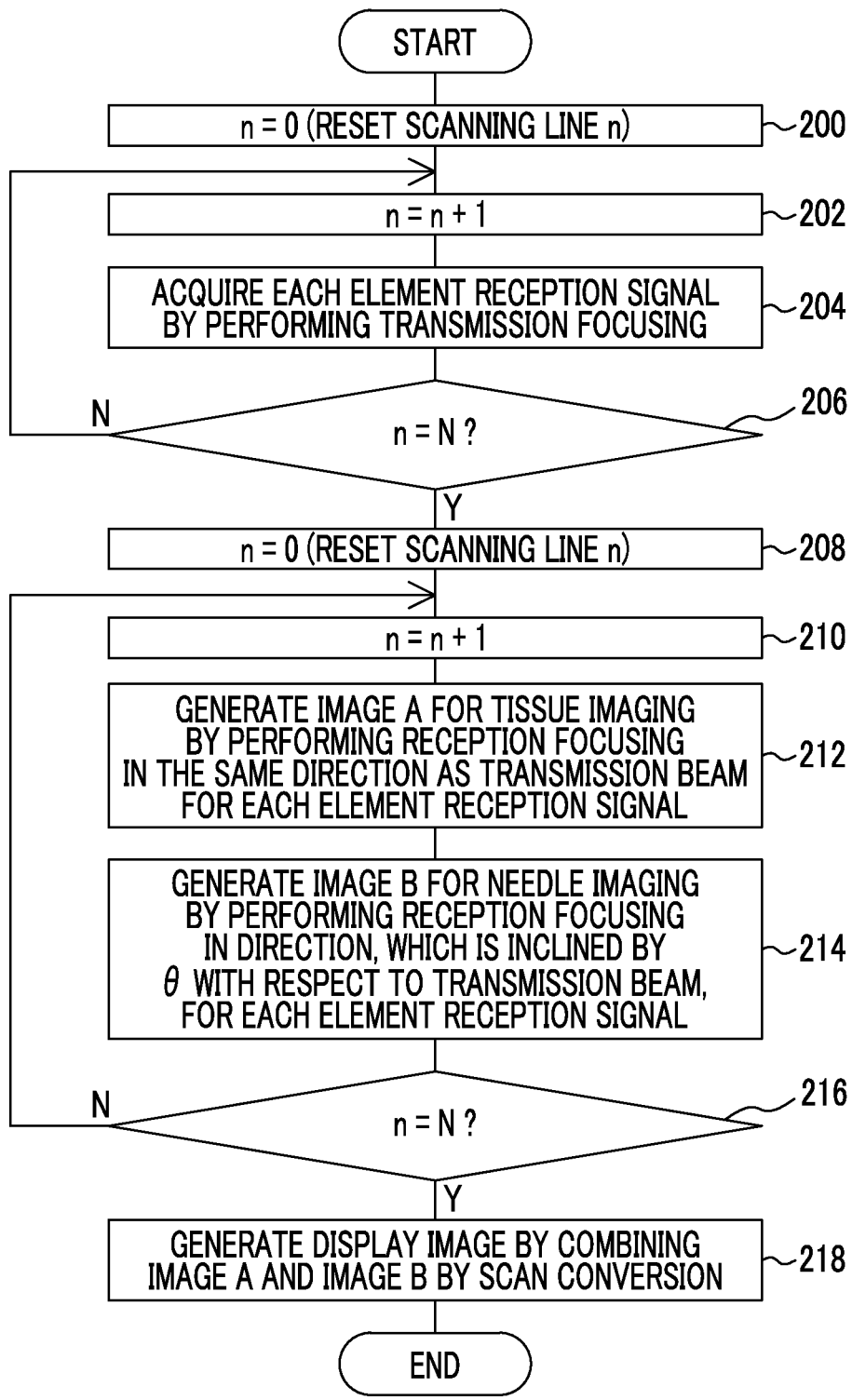

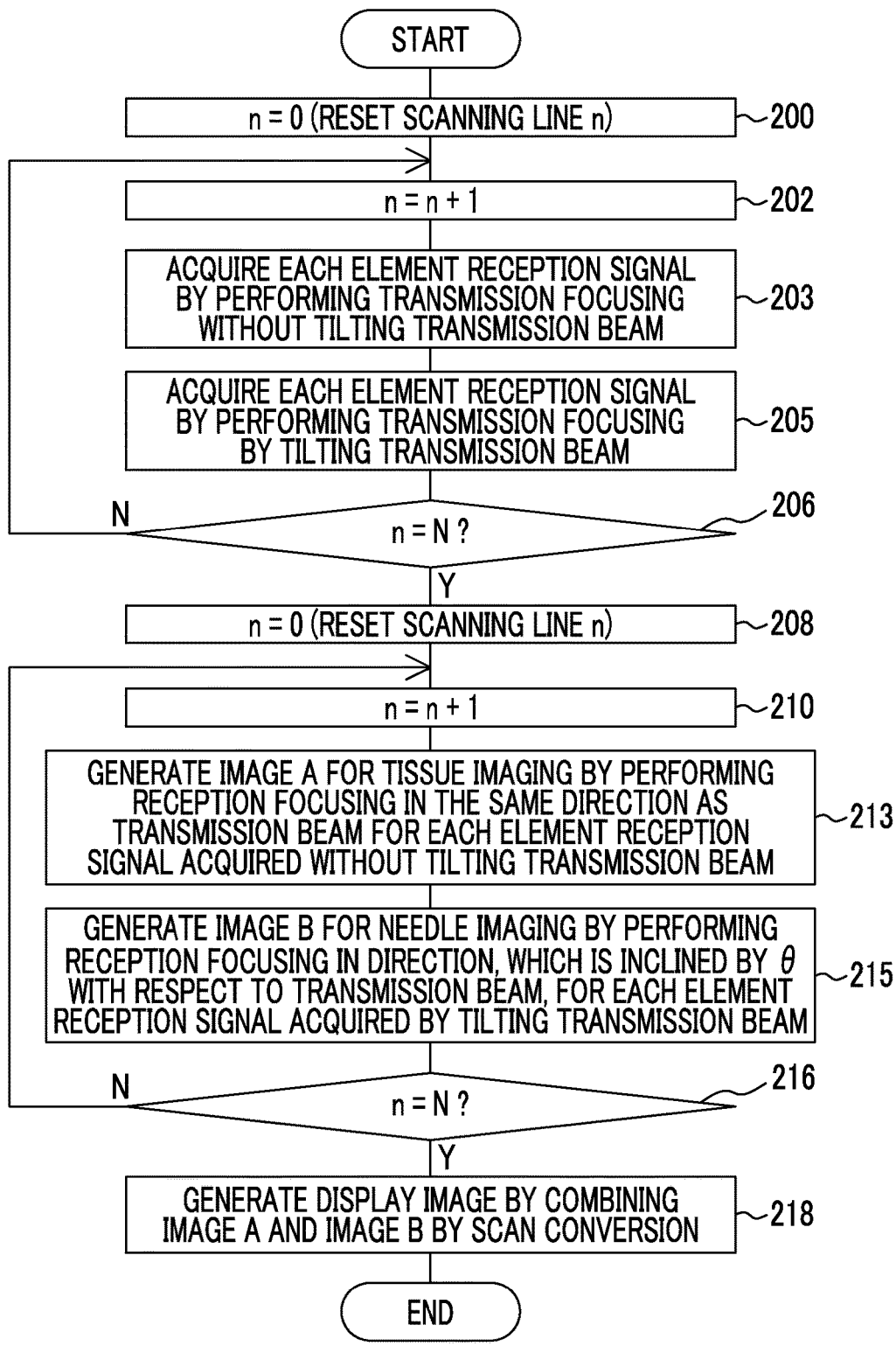

ULTRASOUND DIAGNOSTIC DEVICE, ULTRASOUND DIAGNOSTIC METHOD, AND ULTRASOUND DIAGNOSTIC PROGRAM

CROSS-REFERENCE TO RELATED APPLICATIONS

This application is a continuation application of International Application No. PCT/JP2014/061198, filed on Apr. 21, 2014, the disclosure of which is incorporated herein by reference in its entirety. Further, this application claims priority from Japanese Patent Application No. 2013-157656, filed on Jul. 30, 2013, the disclosure of which is incorporated by reference herein in its entirety.

BACKGROUND

Technical Field

The present disclosure relates to an ultrasound diagnostic device, an ultrasound diagnostic method, and a storage medium storing an ultrasound diagnostic program.

Related Art

When visualizing a needle by the transmission and reception of ultrasound waves, if the angle of the needle becomes an acute angle, the reflection deviates from the reception opening, as shown in FIG. 18A. In this case, it is not possible to receive the reflected wave from the needle. Therefore, as shown in FIG. 18B, a method of receiving the reflected wave from the needle by transmitting a transmission beam obliquely so that the transmission beam is perpendicular to the needle is known.

However, an image generated by tilting the transmission beam is not suitable to see the tissue since the image quality is degraded due to the influence of side lobes or the like.

Therefore, JP2012-213606A proposes that a first ultrasound image is generated by performing ultrasound transmission in a first direction, a second ultrasound image group is generated by transmitting ultrasound waves in a plurality of directions for the purpose of needle imaging, a needle image in which the needle is visualized is generated by analyzing the first image and the second image group or the brightness distribution of the second image group, and the first image and the needle image are combined.

As a method of visualizing the needle image, in addition to the method disclosed in JP2012-213606A, a technique disclosed in JP2010-51379A and the like have also been proposed.

JP2010-51379A proposes that an ultrasound beam having an intensity distribution around a first direction is transmitted from ultrasound transducers of a first group and an ultrasound image in a second direction different from the first direction is generated based on reception signals obtained by the reception of ultrasound echo signals of ultrasound transducers of a second group.

In the technique disclosed in JP2012-213606A, however, one tissue imaging and multiple needle imagings are required. For this reason, the frame rate is reduced.

In addition, in the technique disclosed in JP2010-51379A, a plane wave for which transmission focusing is not required is used. Accordingly, depending on the angle of the needle, reflected waves cannot be obtained at all. As a result, the needle may not be able to be visualized.

The present disclosure has been made in view of the above situation, and provides an ultrasound diagnostic device, an ultrasound diagnostic method, and a non-transitory storage medium storing an ultrasound diagnostic program capable of visualizing a reflector, such as a needle, other than the tissue without lowering the frame rate.

SUMMARY

A first aspect of the present disclosure is an ultrasound diagnostic device including: a probe including plural elements that generate and transmit ultrasound waves and receive ultrasound waves reflected from an inspection target; a transmission unit that transmits ultrasound waves from the plurality of elements so as to transmit an ultrasound beam by forming a transmission focus in a predetermined first direction; and a second reception focusing unit that performs reception focusing for each reception signal received by each element of the probe according to reflection on a path in a second direction other than the first direction, among transmission wave paths of the ultrasound beam transmitted into the inspection target by the transmission unit.

According to the ultrasound diagnostic device of the first aspect, the probe includes plural elements that generate and transmit ultrasound waves and receive ultrasound waves reflected from the inspection target.

The transmission unit transmits ultrasound waves from the plural elements so as to transmit an ultrasound beam by forming a transmission focus in the first direction set in advance.

The second reception focusing unit performs reception focusing for each reception signal received by each element of the probe according to the reflection on the path in the second direction other than the first direction, among the transmission paths of the ultrasound beam transmitted into the inspection target by the transmission unit.

Thus, since the transmission focusing is performed by the transmission unit, ultrasound echoes generated by reflection from the reflection points in directions other than the first direction are also received by the plural elements. Therefore, it is possible to visualize a reflector, such as a needle, by performing reception focusing according to the reflection on the path in the second direction using the second reception focusing unit. In addition, it is also possible to visualize the tissue by performing the reception focusing in the first direction. Therefore, it is possible to visualize a reflector, such as a needle, without lowering the frame rate. That is, by further including a first reception focusing unit that performs reception focusing according to reflection on a path in the first direction, it is possible to visualize the tissue while visualizing a reflector, such as a needle, without lowering the frame rate. In this case, a combination unit that combines results of the reception focusing of the first and second reception focusing units may be further included.

In the first aspect, the transmission unit may transmit ultrasound waves from the plural elements so as to transmit an ultrasound beam by forming a transmission focus in the first direction in each of two or more different openings of the probe, and the second reception focusing unit may perform reception focusing for the reception signal for each opening according to a common reflection point in the second direction.

The second reception focusing unit may perform reception focusing based on a delay time set on the assumption that each transmission wave converges and diverges in a shape of a spherical wave in a shallower region and a deeper region than the transmission focus. The second reception focusing unit may assume specular reflection at each point in the second direction, assume a sound source at a different point from the point, and perform reception focusing for each point in the second direction based on a delay time for the assumed sound source.

The first aspect may further include a determination unit that determines a direction of a needle based on a result of the reception focusing of the second reception focusing unit.

In addition, a designation unit that designates the second direction may be further included. In this case, the designation unit may designate the second direction based on information related to a direction obtained from a fixing portion that fixes a needle. The second direction may be designated based on a result of last reception focusing performed by the second reception focusing unit.

A second aspect of the present disclosure is an ultrasound diagnostic method including: transmitting an ultrasound beam by forming a transmission focus in a predetermined first direction from plural elements of a probe, the prove including the plural elements that generate and transmit ultrasound waves and receive ultrasound waves reflected from an inspection target; and performing second reception focusing for each reception signal received by each element of the probe according to reflection on a path in a second direction other than the first direction, among transmission wave paths of the ultrasound beam transmitted into the inspection target.

According to the ultrasound diagnostic method of the second aspect, ultrasound waves are transmitted from the plural elements of the probe, which includes the plural elements that generate and transmit ultrasound waves and receive ultrasound waves reflected from the inspection target, so as to transmit an ultrasound beam by forming a transmission focus in a first direction set in advance.

In addition, the second reception focusing is performed for each reception signal received by each element of the probe according to the reflection on the path in the second direction other than the first direction, among the transmission wave paths of the ultrasound beam transmitted into the inspection target.

Thus, by performing the transmission focusing, ultrasound echoes generated by reflection from the reflection points in directions other than the first direction are also received by the plural elements. Therefore, it is possible to visualize a reflector, such as a needle, by performing second reception focusing according to the reflection on the path in the second direction. In addition, it is also possible to visualize the tissue by performing the reception focusing in the first direction. Therefore, it is possible to visualize a reflector, such as a needle, without lowering the frame rate. That is, the present disclosure may further include performing first reception focusing according to reflection on a path in the first direction, so that it is possible to visualize the tissue while visualizing a reflector, such as a needle, without lowering the frame rate. In this case, results of the reception focusing of the first reception focusing and the second reception focusing may be combined.

In the second aspect, the ultrasound beam may be transmitted from the plural elements by forming a transmission focus in the first direction in each of two or more different openings of the probe, and reception focusing may be performed for the reception signal for each opening according to a common reflection point in the second direction in the second reception focusing.

In the second reception focusing, reception focusing may be performed based on a delay time set on the assumption that each transmission wave converges and diverges in a shape of a spherical wave in a shallower region and a deeper region than the transmission focus. In addition, specular reflection may be assumed at each point in the second direction, a sound source may be assumed at a different point from the point, and reception focusing may be performed for each point in the second direction based on a delay time for the assumed sound source.

The second aspect may further include determining a direction of a needle based on a result of the second reception focusing.

In addition, a step of designating the second direction may be further included. In this case, the second direction may be designated based on information related to a direction obtained from a fixing portion that fixes a needle. In addition, the second direction may be designated based on a result of the second reception focusing that has been performed last time.

A third aspect of the present disclosure is a non-transitory storage medium storing an ultrasound diagnostic program that causes a computer to execute processing including: transmitting an ultrasound beam by forming a transmission focus in a predetermined first direction from plural elements of a probe, the probe including the plural elements that generate and transmit ultrasound waves and receive ultrasound waves reflected from an inspection target; and performing second reception focusing for each reception signal received by each element of the probe according to reflection on a path in a second direction other than the first direction, among transmission wave paths of the ultrasound beam transmitted into the inspection target.

According to the third aspect, ultrasound waves are transmitted from the plural elements of the probe, which includes the plural elements that generate and transmit ultrasound waves and receive ultrasound waves reflected from the inspection target, so as to transmit an ultrasound beam by forming a transmission focus in a first direction set in advance.

In addition, the second reception focusing is performed for each reception signal received by each element of the probe according to the reflection on the path in the second direction other than the first direction, among the transmission wave paths of the ultrasound beam transmitted into the inspection target in the transmission step.

Thus, by performing the transmission focusing, ultrasound echoes generated by reflection from the reflection points in directions other than the first direction are also received by the plural elements. Therefore, it is possible to visualize a reflector, such as a needle, by performing second reception focusing according to the reflection on the path in the second direction. In addition, it is also possible to visualize the tissue by performing the reception focusing in the first direction. Therefore, it is possible to visualize a reflector, such as a needle, without lowering the frame rate. That is, the present disclosure may further include performing first reception focusing according to reflection on a path in the first direction, so that it is possible to visualize the tissue while visualizing a reflector, such as a needle, without lowering the frame rate. In this case, results of the reception focusing of the first reception focusing and the second reception focusing may be combined.

In the third aspect, the ultrasound beam may be transmitted from the plural elements by forming a transmission focus in the first direction in each of two or more different openings of the probe, and second reception focusing may be performed for the reception signal for each opening according to a common reflection point in the second direction.

In the second reception focusing, reception focusing may be performed based on a delay time set on the assumption that each transmission wave converges and diverges in a shape of a spherical wave in a shallower region and a deeper region than the transmission focus. In addition, specular reflection may be assumed at each point in the second direction, a sound source may be assumed at a different point from the point, and reception focusing may be performed for each point in the second direction based on a delay time for the assumed sound source.

The processing of the third aspect may further include determining a direction of a needle based on a result of the second reception focusing.

In addition, designating the second direction may be further included. In this case, the second direction may be designated based on information regarding a direction obtained from a fixing portion that fixes a needle. In addition, the second direction may be designated based on a result of the second reception focusing that has been performed last time.

As described above, according to the present aspects, it is possible to visualize a reflector, such as a needle, other than the tissue without lowering the frame rate.

BRIEF DESCRIPTION OF THE DRAWINGS

FIG. 4 is a block diagram showing the schematic configuration of a phasing addition/detection processing section in the ultrasound diagnostic device according to the first embodiment of the present disclosure.

FIG. 10 is a flowchart showing an example of the flow of the process performed by the main part of the ultrasound diagnostic device 10 according to the second embodiment of the present disclosure.

FIG. 13 is a flowchart showing an example of the flow of the process performed by the main part of the ultrasound diagnostic device according to the third embodiment of the present disclosure.

DESCRIPTION OF THE PREFERRED EMBODIMENTS

Hereinafter, an example of an embodiment of the present disclosure will be described with reference to the respective diagrams.

(First Embodiment)

Figure 1:
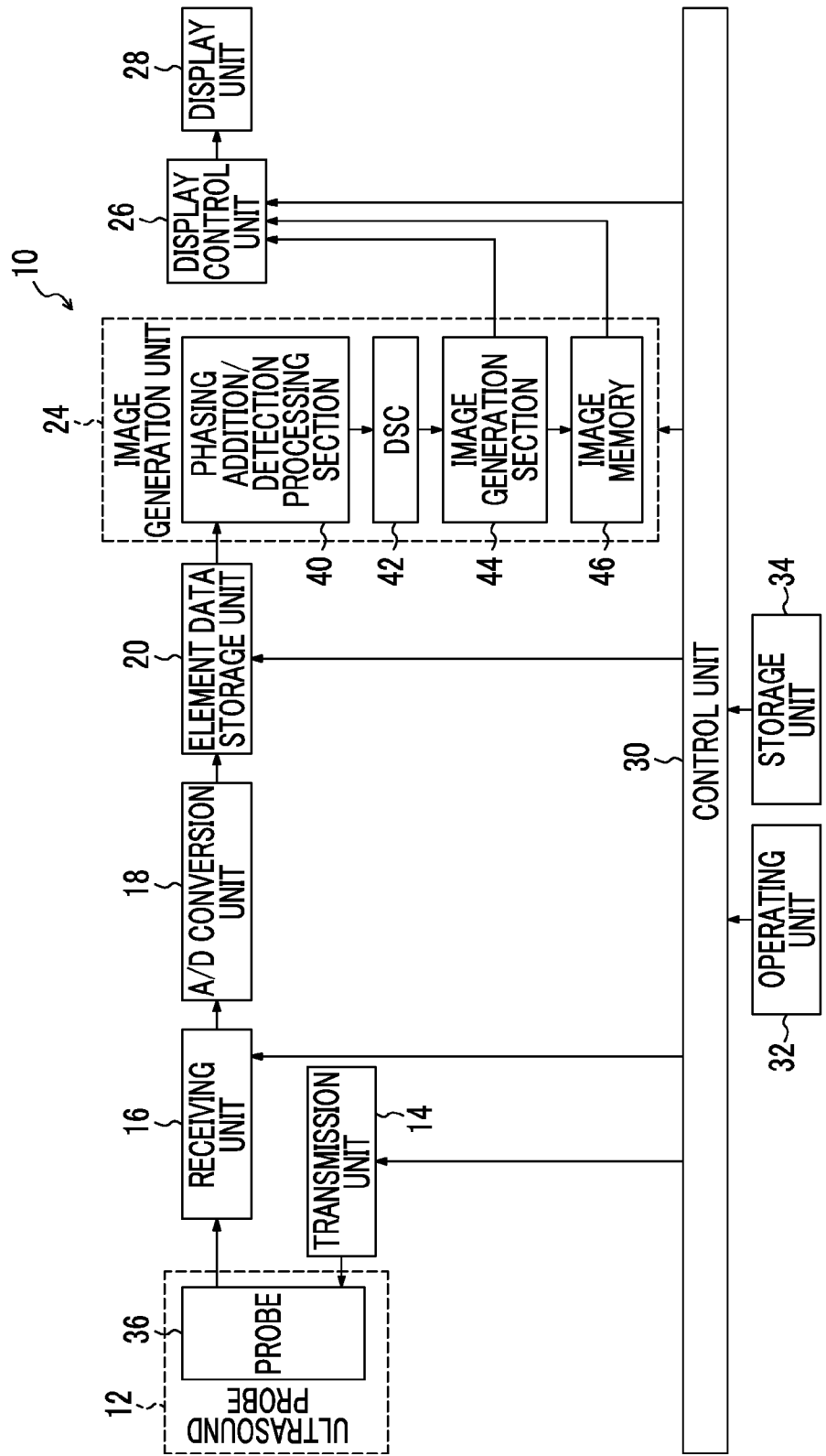
FIG. 1 is a block diagram showing the schematic configuration of an ultrasound diagnostic device according to a first embodiment of the present disclosure.

FIG. 1 is a block diagram showing the schematic configuration of an ultrasound diagnostic device according to a first embodiment of the present disclosure.

As shown in FIG. 1, an ultrasound diagnostic device 10 includes an ultrasound probe 12, a transmission unit 14 and a receiving unit 16 that are connected to the ultrasound probe 12, an A/D conversion unit 18, an element data storage unit 20, an image generation unit 24, a display control unit 26, a display unit 28, a control unit 30, an operating unit 32, and a storage unit 34.

The ultrasound probe 12 has a probe 36 that is used in a normal ultrasound diagnostic device. The probe 36 includes plural elements, that is, ultrasound transducers arranged in a one-dimensional or two-dimensional array. When capturing an ultrasound image of a subject, each of the ultrasound transducers transmits an ultrasound beam to the subject according to a driving signal supplied from the transmission unit 14, and receives an ultrasound echo from the subject and outputs a reception signal. In the present embodiment, each of a predetermined number of ultrasound transducers that form a set of the plural ultrasound transducers of the probe 36 generates each component of one ultrasound beam, and a set of a predetermined number of ultrasound transducers generates one ultrasound beam to be transmitted to the subject.

For example, each ultrasound transducer is formed by an element (transducer) in which electrodes are formed at both ends of the piezoelectric body including piezoelectric ceramic represented by lead zirconate titanate (PZT), a polymer piezoelectric element represented by polyvinylidene fluoride (PVDF), piezoelectric single crystal represented by lead magnesium niobate-lead titanate (PMN-PT), or the like. That is, the probe 36 is a transducer array in which plural transducers are arranged in a one-dimensional or two-dimensional array as plural ultrasound elements.

When a pulsed or continuous-wave voltage is applied to the electrodes of such a transducer, the piezoelectric body expands and contracts to generate pulsed or continuous-wave ultrasound waves from each transducer. By combination of these ultrasound waves, an ultrasound beam is formed. In addition, the respective transducers expand and contract by receiving the propagating ultrasound waves, thereby generating electrical signals. These electrical signals are output as reception signals of the ultrasound waves.

The transmission unit 14 includes, for example, plural pulsers. Based on a transmission delay pattern selected according to the control signal from the control unit 30, the transmission unit 14 adjusts the amount of delay of the driving signal of each ultrasound element so that the ultrasound beam components transmitted from plural ultrasound transducers (hereinafter, referred to as ultrasound elements) of the probe 36 form one ultrasound beam, and supplies the adjusted driving signals to the plural ultrasound elements that form a set. Accordingly, ultrasound waves are transmitted from the plural ultrasound elements, transmission focusing is performed to generate an ultrasound beam, and the ultrasound beam is transmitted.

According to the control signal from the control unit 30, the receiving unit 16 receives an ultrasound echo, which is generated by the interaction between the ultrasound beam and the subject, from the subject using each ultrasound element of the probe 36, amplifies the reception signal, that is, an analog element signal of each ultrasound element, and supplies the amplified analog element signal to the A/D conversion unit 18.

The A/D conversion unit 18 is connected to the receiving unit 16, and converts the analog element signal supplied from the receiving unit 16 into digital element data. The A/D conversion unit 18 supplies the A/D-converted digital element data to the element data storage unit 20.

The element data storage unit 20 stores the digital element data output from the A/D conversion unit 18 in a sequential manner. In addition, the element data storage unit 20 stores information regarding the frame rate input from the control unit 30 (for example, parameters indicating the depth of the reflection position of an ultrasound wave, the density of scanning lines, and a field-of-view width) so as to be associated with the above digital element data (hereinafter, simply referred to as element data).

Under the control of the control unit 30, the image generation unit 24 generates an acoustic ray signal (reception data) from the element data stored in the element data storage unit 20, and generates an ultrasound image from the acoustic ray signal. Specifically, the image generation unit 24 includes a phasing addition/detection processing section 40, a DSC 42, an image generation section 44, and an image memory 46.

The phasing addition/detection processing section 40 performs reception focusing processing by selecting one reception delay pattern from plural reception delay patterns stored in advance according to the receiving direction set by the control unit 30, applying each delay to the element data based on the selected reception delay pattern, and adding up the results. Through the reception focusing processing, reception data (acoustic ray signal) with a narrowed focus of the ultrasound echo is generated.

The phasing addition/detection processing section 40 generates B-mode image data, which is tomographic image information regarding a tissue within the subject, by correcting the attenuation due to the distance according to the depth of the reflection position of the ultrasound wave and then performing envelope detection processing for the reception data generated by the reception focusing processing.

The digital scan converter (DSC) 42 converts the B-mode image data generated by the detection processing section 40 into image data according to the normal television signal scanning method (raster conversion).

The image generation section 44 generates B-mode image data to be supplied for inspection or display by performing various kinds of required image processing, such as gradation processing, on the B-mode image data input from the DSC 42, and outputs the generated B-mode image data for inspection or display to the display control unit 26 in order to display the generated B-mode image data or stores the generated B-mode image data for inspection or display in the image memory 46.

The image memory 46 temporarily stores the B-mode image data for inspection generated by the image generation section 44. The B-mode image data for inspection stored in the image memory 46 is read out to the display control unit 26, when necessary, so as to be displayed on the display unit 28.

The display control unit 26 displays an ultrasound image on the display unit 28 based on the B-mode image signal for inspection having been subjected to image processing by the image generation section 44.

The display unit 28 includes, for example, a display device, such as an LCD, and displays an ultrasound image under the control of the display control unit 26.

The control unit 30 controls each unit of the ultrasound diagnostic device 10 based on a command that is input from the operating unit 32 by the operator.

When various kinds of information, especially, information required to calculate the delay time used in the phasing addition/detection processing section 40 of the image generation unit 24 has been input through the operating unit 32 by the operator, the control unit 30 supplies the above-described various kinds of information input through the operating unit 32 to the respective units, such as the transmission unit 14, the receiving unit 16, the element data storage unit 20, the image generation unit 24, and the display control unit 26, when necessary.

The operating unit 32 is used when the operator performs an input operation, and includes a keyboard, a mouse, a trackball, a touch panel, and the like.

The operating unit 32 includes an input device used when the operator inputs various kinds of information, especially, information regarding plural ultrasound elements of the probe 36 of the probe 12 used for the delay time calculation described above, the speed of sound in an inspection target region of the subject, a focal position of the ultrasound beam, and a transmission opening and a reception opening of the probe 36, when necessary.

The storage unit 34 stores various kinds of information input through the operating unit 32, especially, the above information regarding the probe 12, the speed of sound, the focal position, and the transmission opening and the reception opening, information required for the processing or operation of each unit controlled by the control unit 30, such as the transmission unit 14, the receiving unit 16, the element data storage unit 20, the image generation unit 24, and the display control unit 26, an operation program or a processing program for executing the processing or operation of each unit, and the like. As the storage unit 34, recording media, such as a hard disk, a flexible disk, an MO, an MT, a RAM, a CD-ROM, and a DVD-ROM, can be used.

The phasing addition/detection processing section 40, the DSC 42, the image generation section 44, and the display control unit 26 may be configured by a CPU and an operation program causing the CPU to perform various kinds of processing, or a hardware configuration, such as a digital circuit, may be used therefor.

Figure 2A:
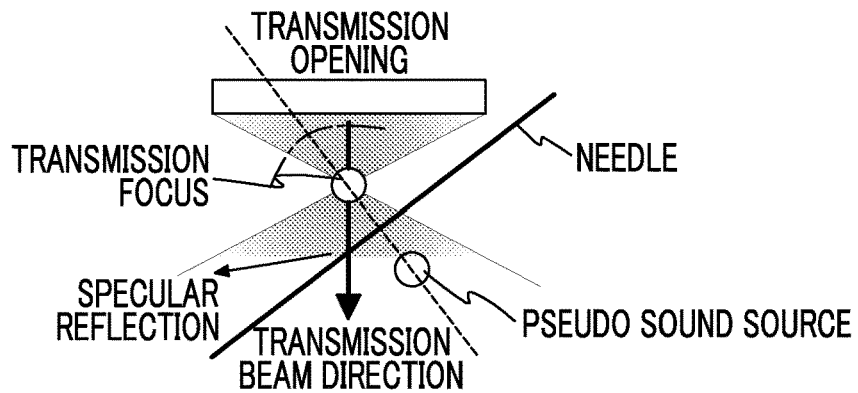
FIG. 2A is a diagram for explaining specular reflection by the needle for each depth of the transmission focus, and is a diagram showing a case in which the transmission focus is shallower than the needle.
Figure 2B:
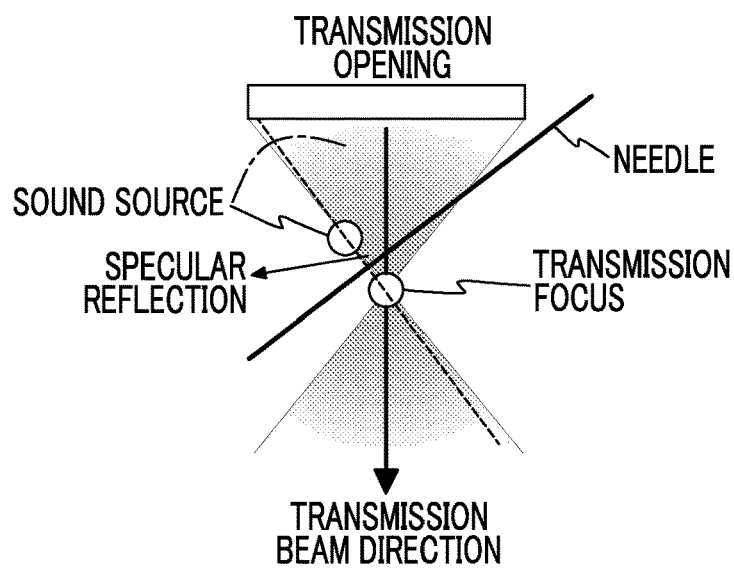
FIG. 2B is a diagram for explaining specular reflection by the needle for each depth of the transmission focus, and is a diagram showing a case in which the transmission focus is deeper than the needle.
Figure 2C:
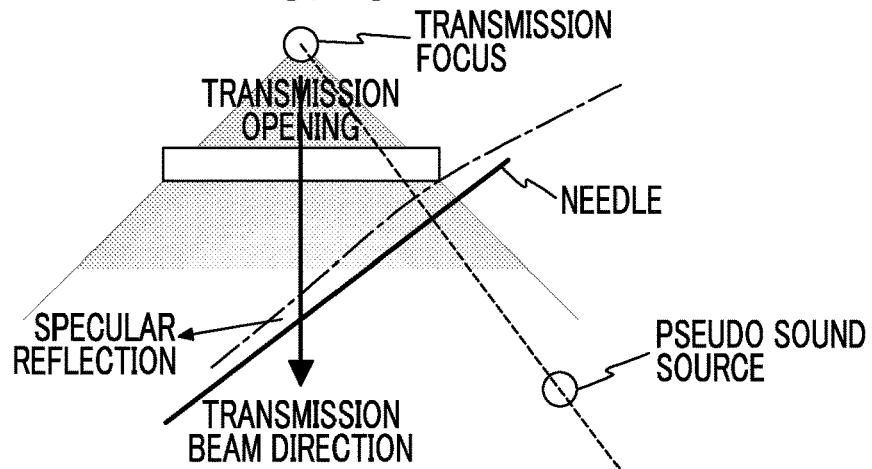
FIG. 2C is a diagram for explaining specular reflection by the needle for each depth of the transmission focus, and is a diagram showing a case in which the transmission focus is located behind the opening.

Incidentally, in the ultrasound diagnostic device 10 configured as described above, the ultrasound beam is transmitted by performing transmission focusing, and acoustic waves (ultrasound beams) formed by transmission focusing propagate in various directions in a shallower or deeper region than the transmission focus. Accordingly, even if the specular reflection by the needle in the transmission beam direction deviates from the reception opening, the specular reflection of acoustic waves in directions other than the transmission beam direction due to the needle is captured in the reception opening, as shown by the one-dot chain line in FIGS. 2A to 2C. The reflection of the acoustic wave, which is formed by transmission focusing, by the needle is equivalent to a case in which there is a focus at the symmetrical position of the focus formed by transmission focusing with the needle as a specular reflection surface. Therefore, if the transmission focus is regarded as a pseudo sound source, as shown in FIGS. 2A and 2C, reflection equivalent to the acoustic wave when a pseudo sound source is present at the symmetrical position of the transmission focus with respect to the needle is caught in the reception opening. In the case shown in FIG. 2B, a sound source is actually formed. However, since the reflection spread range is determined by the directivity of an element, transmission opening, depth, frequency, or the like, the reflection does not necessarily spread in all directions. Accordingly, the above-described pseudo sound source or the reflected wave equivalent to the sound source cannot necessarily be captured. That is, the spread range of the acoustic wave in a shallower or deeper region than the transmission focus is determined by the transmission opening, depth, frequency, or the like, and reflection spreads only to a range interposed in the direction of specular reflection by the needle in a direction at both the ends. The specular reflection in the transmission beam direction can be regarded as a part of the reflection.

Figure 3A:
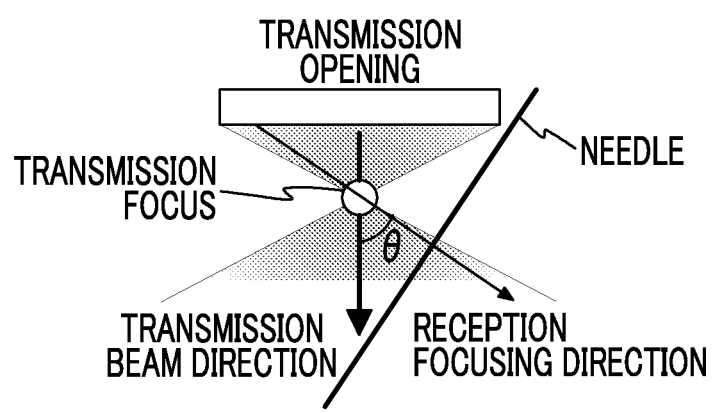
FIG. 3A is a diagram showing an example of performing reception focusing according to the reflection on the path in a direction other than the transmission beam direction, and is a diagram showing a case in which the transmission focus is shallower than the needle.
Figure 3B:
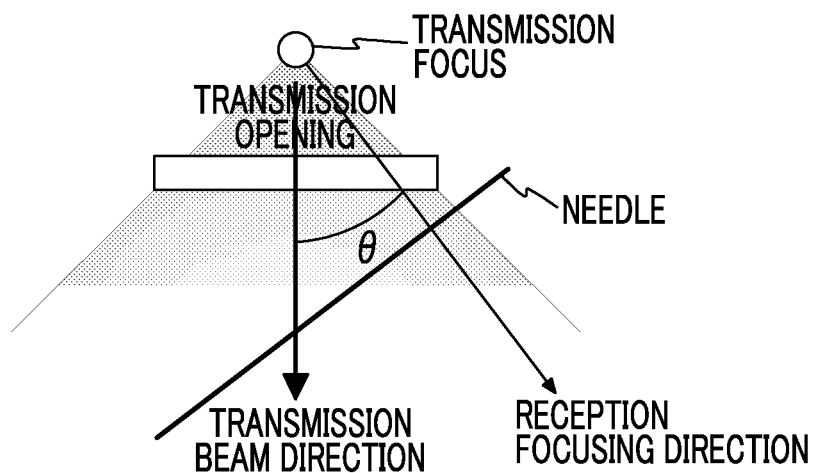
FIG. 3B is a diagram showing an example of performing reception focusing according to the reflection on the path in a direction other than the transmission beam direction, and is a diagram showing a case in which the transmission focus is located behind the opening.

Therefore, in the ultrasound diagnostic device 10 according to the present embodiment, focusing on the fact that the acoustic wave of the ultrasound beam formed by transmission focusing also propagates in directions other than the transmission beam direction, the reflector, such as a needle, other than the tissue can be satisfactorily visualized by performing reception focusing for each reception signal, which is received by each ultrasound element of the probe 36, according to the reflection on the path in a direction other than the transmission beam direction, as shown in FIGS. 3A and 3B. In the present embodiment, the reception focusing is performed based on the delay time set on the assumption that transmission waves converge and diverge in the shape of a spherical wave in a shallower region and a deeper region than the transmission focus.

In the present embodiment, the phasing addition/detection processing section 40 is configured to perform the reception focusing according to the reflection on the path in a direction other than the transmission beam direction. FIG. 4 is a block diagram showing the schematic configuration of the phasing addition/detection processing section 40 in the ultrasound diagnostic device 10 according to the first embodiment of the present disclosure.

Specifically, as shown in FIG. 4, the phasing addition/detection processing section 40 includes a first reception focusing section 40A, a second reception focusing section 40B, a first detection processing section 40C, a second detection processing section 40D, and a combination processing section 40E.

The first reception focusing section 40A performs reception focusing by selecting one reception delay pattern from plural reception delay patterns stored in advance for the transmission direction (vertical direction in the present embodiment) of the ultrasound beam, applying each delay to the element data based on the selected reception delay pattern, and adding up the results.

The second reception focusing section 40B performs reception focusing so as to be inclined by the angle θ from the transmission focus with respect to the transmission direction (vertical direction) of the ultrasound beam.

Here, a reception focus that is inclined by the angle θ with respect to the transmission direction will be described with reference to FIGS. 5A to 5C.

Figure 5A:
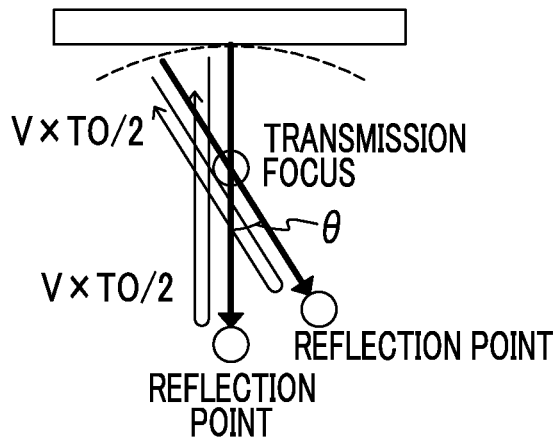
FIG. 5A is a diagram for explaining reception focusing performed by a second reception focusing section in the ultrasound diagnostic device according to the first embodiment of the present disclosure.

As shown in FIG. 5A, when the transmission beam is vertical, the depth of the reflection point is given by V×T0/2. The depth of the reflection point in a direction inclined by θ with respect to the vertical direction is also given by V×T0/2. Here, T0 indicates a reciprocating ultrasound wave propagation time in a vertical direction or in a direction inclined by θ with respect to the vertical direction, and V indicates the speed of sound.

Figure 5B:
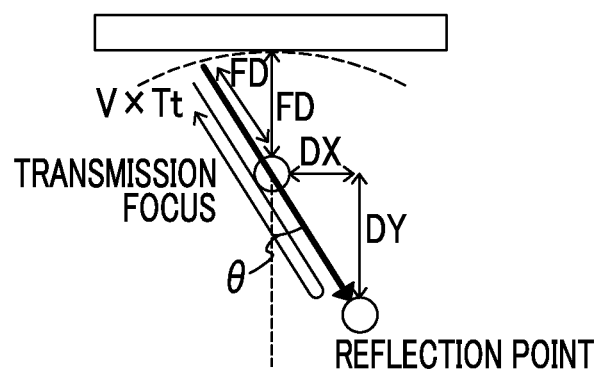
FIG. 5B is a diagram for explaining reception focusing performed by the second reception focusing section in the ultrasound diagnostic device according to the first embodiment of the present disclosure.

Then, it can be seen from FIG. 5B that the distances DX and DY of the reflection point from the transmission focus in the θ direction are given by the following equations. Here, FD indicates the depth of the transmission focus.

$$DX = (V \times Tt - FD) \times \sin(\theta)$$

$$DY = (V \times Tt - FD) \times \cos(\theta)$$

$$Tt = T0/2$$

Figure 5C:
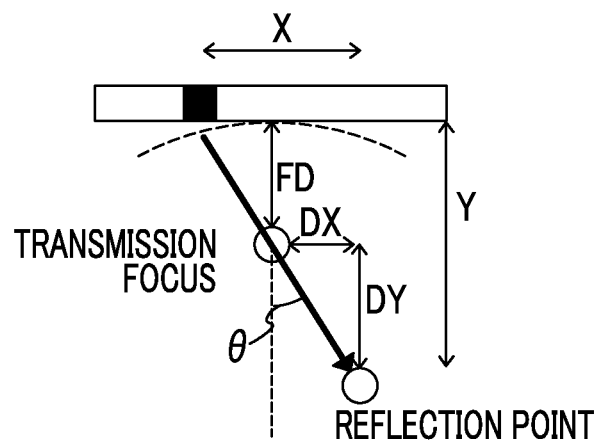
FIG. 5C is a diagram for explaining reception focusing performed by the second reception focusing section in the ultrasound diagnostic device according to the first embodiment of the present disclosure.

Then, it can be seen from FIG. 5C that the distances X and Y of the reflection point from the j-th element from the center of the opening are given by the following equations.

$$X = DX - j \times EP$$

$$Y = DY + FD$$

Here, EP is a gap between elements, and j is a positive or negative value with an element at the center as 0.

Therefore, it can be seen that the propagation time of the acoustic wave returning to the j-th element from the reflection point is given by the following equation.

$$Tr = \mathrm{sqrt}(X^2 + Y^2)/V$$

The ultrasound wave transmitted from the opening is reflected at the reflection point after Tt, and returns to the j-th element after Tr. That is, the reflected wave from the reflection point returns to the j-th element after T=Tt+Tr from the transmission.

Therefore, by adding up the signals of the respective elements using the following equation, it is possible to extract the reflected wave from the reflection point, that is, it is possible to perform reception focusing.

$$RF(i, T0) = \Sigma ELE(i, j, T)$$

Here, i indicates a scanning line to which the opening corresponds, ELE(i, j, T) indicates a signal at time T of an element j of the scanning line i, and RF(i, T0) indicates an RF signal at time T0 (equivalent to depth) in the θ direction of the scanning line i after reception focusing.

That is, reception focusing that is inclined by the angle θ with respect to the transmission direction is performed so as to satisfy the following equations.

$$RF(i, T0) = \Sigma ELE(i, j, T)$$

$$T = Tt + Tr$$

$$Tr = \mathrm{sqrt}(X^2 + Y^2)/V$$

$$X = DX - j \times EP$$

$$Y = DY + FD$$

$$DX = (V \times Tt - FD) \times \sin(\theta)$$

$$DY = (V \times Tt - FD) \times \cos(\theta)$$

$$Tt = T0/2$$

Here, RF(i, T0): RF signal of the i-th scanning line at time T0. The time of the moment of transmission is set to 0.

ELE(i, j, T): data at time T of the j-th element of the element signal acquired by transmission corresponding to the i-th scanning line. Here, j is 0 in the case of an element corresponding to the i-th scanning line position, and is a positive or negative value.

Σ: integration on j

Tt: time until the transmission wave reaches a reflection point

Tr: time until the reflected wave reaches an element

V: speed of sound

EP: gap between elements

FD: depth of transmission focus

θ: angle of the reception focusing direction that is inclined with respect to the transmission direction As shown in FIG. 3B, when forming a transmission focus behind the transmission opening, the depth FD of the transmission focus is negative.

On the other hand, the first detection processing section 40C generates B-mode image data, which is tomographic image information regarding a tissue within the subject, by correcting the attenuation due to the distance according to the depth of the reflection position of the ultrasound wave and then performing envelope detection processing for the reception data generated by the first reception focusing section 40A.

Similarly, the second detection processing section 40D generates B-mode image data, which is image information regarding a reflector, such as a needle, by correcting the attenuation due to the distance according to the depth of the reflection position of the ultrasound wave and then performing envelope detection processing for the reception data generated by the second reception focusing section 40B.

Then, the combination processing section 40E performs processing for combining the B-mode image data (image A) generated by the first detection processing section 40C and the B-mode image data (image B) generated by the second detection processing section 40D. Specifically, since RF(i, T0) generated by the above-described equation is inclined by the angle θ with respect to the vertical direction, coordinate transformation (scan conversion) is performed so as to match the coordinates of the image A and the image B and the image A and the image B are added up in a predetermined ratio to generate a display image. In this case, the processing may be performed by performing gradation conversion for emphasis as many as the number of high-brightness pixels of the image B, or by extracting only the high-brightness pixels as a needle, or by extracting only the pixels in a predetermined range, or by detecting a straight line by the Hough transform or the like and extracting only the pixels around the detected straight line. In addition, processing for color conversion, chroma conversion, or the like may be further performed according to the brightness of the image A and the image B.

Here, even if the direction of the reception focus by the second reception focusing section 40B is not necessarily perpendicular to the needle, it is possible to visualize the needle as long as the direction of specular reflection by the needle in the direction of the reception focus does deviate from the reception opening. That is, since the specular reflection from the needle is a result of integrating the reflection from each point on the needle, it is possible to capture and visualize a part of specular reflection by the needle by the reception focusing according to the reflection point on the needle as long as the integration result is not zero (specular reflection does not deviate from the reception opening). This is the same as the reason that extraction is possible even if the needle is not horizontal in the ultrasound image generated with both the transmission beam direction and the reception beam direction as vertical directions.

The reception focusing direction of each of the first reception focusing section 40A and the second reception focusing section 40B may be designated by operating the operating unit 32 or the like, or may be designated by acquiring information regarding a direction obtained from the jig for fixing the needle. Alternatively, a current reception focusing direction may be designated based on the result of the last reception focusing.

Subsequently, the operation of the ultrasound diagnostic device 10 according to the first embodiment of the present disclosure and a method of generating an ultrasound image will be described.

Figure 6:
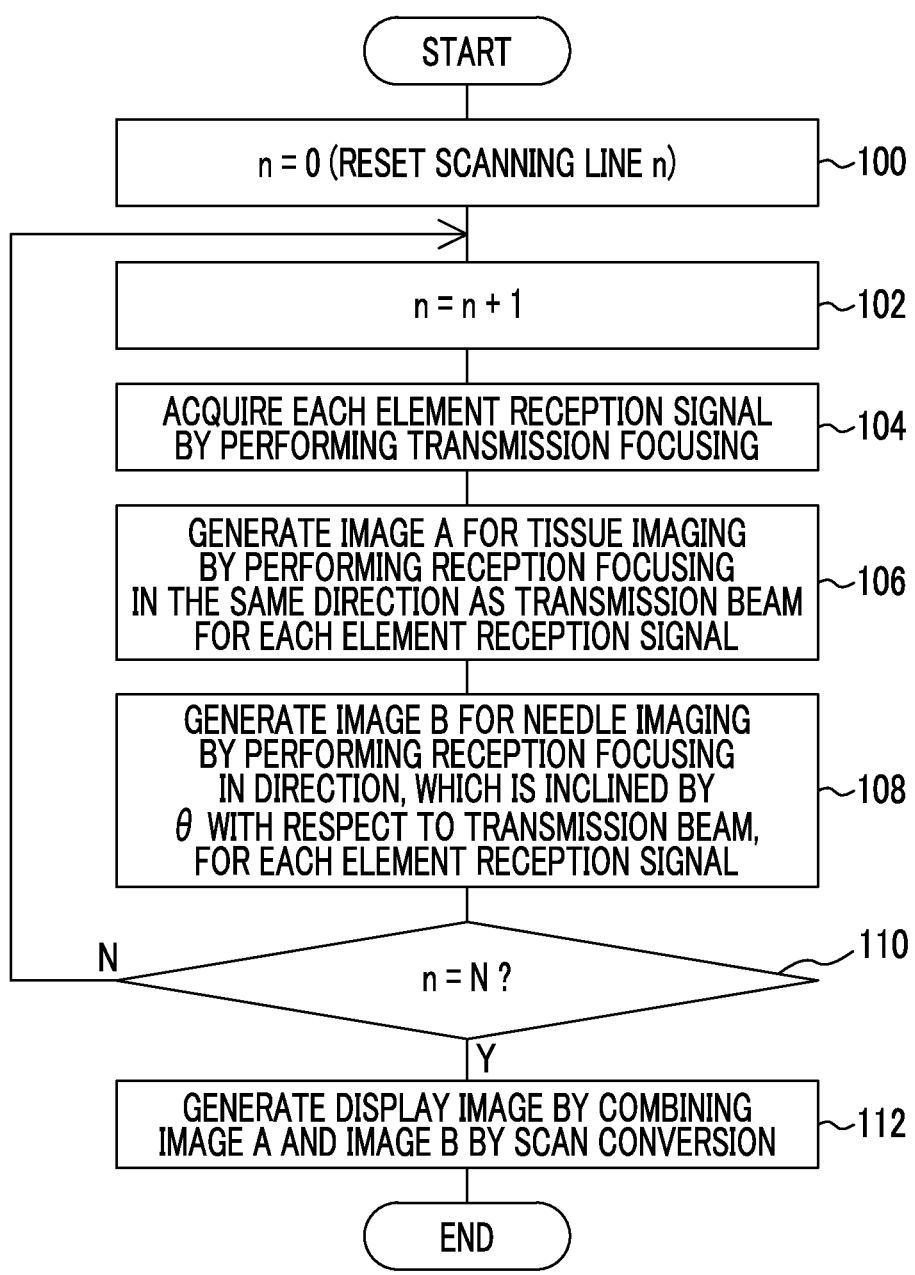
FIG. 6 is a flowchart showing an example of the flow of the process performed by the main part of the ultrasound diagnostic device according to the first embodiment of the present disclosure.

FIG. 6 is a flowchart showing an example of the flow of the process performed by the main part of the ultrasound diagnostic device 10 according to the first embodiment of the present disclosure.

In step 100, a scanning line n is reset (n=0), and the process proceeds to step 102. In step 102, the scanning line n is incremented by 1 (n=n+1), and the process proceeds to step 104.

In step 104, transmission focusing is performed to acquire each element reception signal, and the process proceeds to step 106. That is, when the operator brings the ultrasound probe 12 into contact with the surface of the subject to start measurement, an ultrasound beam is transmitted from the probe 36 according to the driving signal supplied from the transmission unit 14. Then, the ultrasound echo generated by interaction between the transmitted ultrasound beam and the subject is received by the probe 36, the analog element signal is amplified by the receiving unit 16, the amplified analog element signal is converted into digital element data by the A/D conversion unit 18, and the digital element data is stored in the element data storage unit 20.

In step 106, the image A for tissue imaging is generated by performing reception focusing in the same direction as the transmission beam for the reception signal of each element, and the process proceeds to step 108. That is, the first reception focusing section 40A acquires each element reception signal from the element data storage unit 20 and generates reception data (acoustic ray signal) by performing reception focusing in the vertical direction, and the first detection processing section 40C generates a B-mode image signal of the image A for tissue imaging by processing the acoustic ray signal.

In step 108, the image B for needle imaging is generated by performing reception focusing in a direction, which is inclined by the angle θ with respect to the transmission beam, for the reception signal of each element, and the process proceeds to step 110. That is, the second reception focusing section 40B acquires each element reception signal from the element data storage unit 20 and generates reception data (acoustic ray signal) by performing reception focusing in a direction that is inclined by the angle θ with respect to the vertical direction, and the second detection processing section 40D generates a B-mode image signal of the image B for needle imaging by processing the acoustic ray signal.

In step 110, it is determined whether or not n=N. That is, it is determined whether or not the above processing has ended for all the scanning lines. When the determination is negative, the process proceeds to step 102 to repeat the above processing. When the determination is positive, the process proceeds to step 112.

In step 112, the combination processing section 40E generates a display image of one frame by combining the image A and the image B, which have been generated as described above, by scan conversion, and the series of processes are ended. A display image of the next frame is generated by performing the process from the processing of step 100.

Thus, the ultrasound diagnostic device 10 according to the first embodiment of the present disclosure generates an ultrasound beam by performing transmission focusing, receives an ultrasound signal, generates an image for tissue imaging by performing reception focusing in the transmission direction, and generates an image for reflector (needle) imaging other than the tissue by performing reception focusing in a different direction from the transmission direction. Therefore, it is possible to visualize a reflector other than the tissue by one ultrasound transmission.

In the first embodiment described above, the second reception focusing section 40B performs reception focusing in a direction that is inclined by the angle θ with respect to the vertical direction. As shown in FIGS. 2A to 2C, in consideration of the fact that the reflected wave from the needle becomes an acoustic wave equivalent to a case in which a sound source is present at the symmetrical position with the needle as a specular reflection surface, the reception focusing may be performed.

Here, a case in which reception focusing is performed in consideration of the fact that the reflected wave from the needle becomes an acoustic wave equivalent to a case in which a sound source is present at the symmetrical position with the needle as a specular reflection surface will be described with reference to FIGS. 7A and 7B.

Figure 7A:
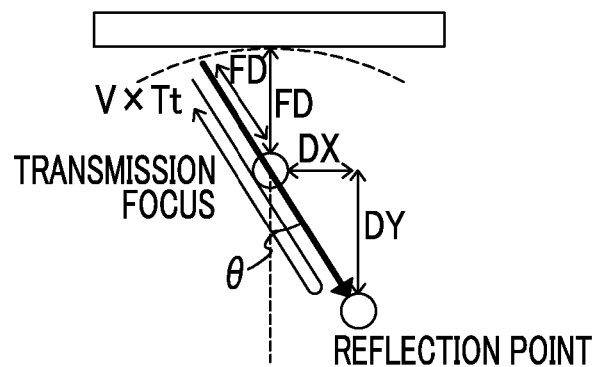
FIG. 7A is a diagram for explaining reception focusing performed by the second reception focusing section in the ultrasound diagnostic device according to the first embodiment of the present disclosure (when an acoustic wave equivalent to a case in which a sound source is present at the symmetrical position with the needle as a specular reflection surface is taken into consideration).

First, calculating DX and DY from FIG. 7A using the following equations is the same as that described above.

$$DX=(V \times Tt-FD) \times \sin(\theta)$$

$$DY=(V \times Tt-FD) \times \cos(\theta)$$

$$Tt=T0/2$$

Figure 7B:
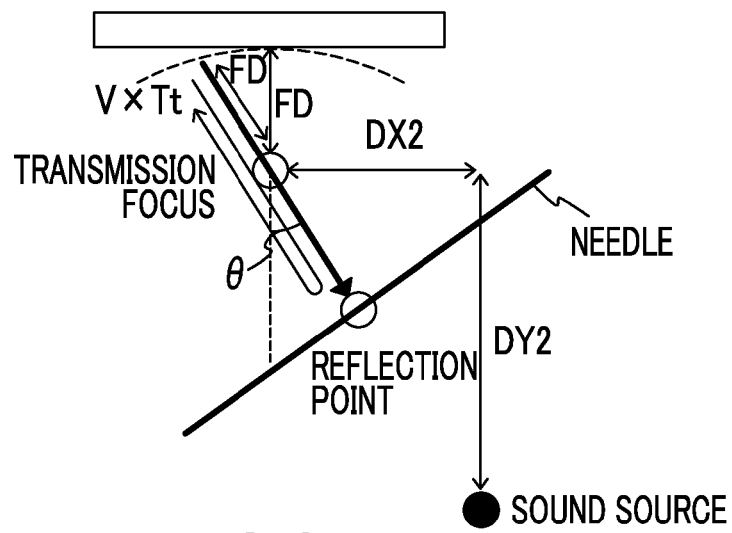
FIG. 7B is a diagram for explaining reception focusing performed by the second reception focusing section in the ultrasound diagnostic device according to the first embodiment of the present disclosure (when an acoustic wave equivalent to a case in which a sound source is present at the symmetrical position with the needle as a specular reflection surface is taken into consideration).

Then, as shown in FIG. 7B, a needle passing through the reflection point is assumed, and a pseudo sound source is assumed at the symmetrical position of the transmission focus. Distances DX2 and DY2 from the transmission focus to the sound source are given by the following equations.

$$DX2=2 \times DX$$

$$DY2=2 \times DY$$

Distances X and Y of the sound source from the j-th element are given by the following equations.

$$X = DX2 - j \times EP$$

$$Y = DY2 + FD$$

The propagation time of the acoustic wave returning to the j-th element from the sound source is given by the following equation.

$$Tr = \operatorname{sqrt}(X^2 + Y^2)/V$$

Time until the transmission focus is formed from the transmission of the ultrasound wave from the opening is FD/V, and it is thought that propagation from the pseudo sound source to the j-th element starts at that moment. Accordingly, it is thought that the reflected wave from the reflection point returns to the j-th element after T=FD/V+Tr from the transmission of the ultrasound wave from the opening.

Therefore, by adding up the signals of the respective elements using the following equation, it is possible to extract the reflected wave from the reflection point, that is, it is possible to perform reception focusing.

$$RF(i, T0) = \Sigma ELE(i, j, T)$$

That is, when performing reception focusing in consideration of the fact that the reflected wave from the needle becomes an acoustic wave equivalent to a case in which a sound source is present at the symmetrical position with the needle as a specular reflection surface, the reception focusing is performed so as to satisfy the following equations.

$$RF(i, T0) = \Sigma ELE(i, j, T)$$

$$T = FD/V + Tr$$

$$Tr = \operatorname{sqrt}(X^2 + Y^2)/V$$

$$X = DX2 - j \times EP$$

$$Y = DY2 + FD$$

$$DX2 = 2 \times DX$$

$$DY2 = 2 \times DY$$

$$DX = (V \times Tt - FD) \times \sin(\theta)$$

$$DY = (V \times Tt - FD) \times \cos(\theta)$$

$$Tt = T0/2$$

The difference from the equations of the reception focusing in the second reception focusing section 40B of the first embodiment described above is that a needle passing through the reflection point in a vertical direction with the angle θ is assumed, a sound source of DX2 and DY2 is assumed as a symmetrical position of the transmission focus with respect to the needle, and the time of propagation to each element from the assumed sound source is calculated and that the time FD/V until the transmission focus is formed is added by regarding the assumed sound source as being formed at the same time as the formation of the transmission focus.

By performing the reception focusing in this manner, it is possible to perform the reception focusing according to the specular reflection from the needle. Therefore, it is possible to visualize the needle better than in the first embodiment. However, by performing reception focusing according to the specular reflection, which is an integration result including ambient reflection, as well as the focused reflection, the reception focusing is also performed on the ambient reflection. Accordingly, even if the focused reflection deviates from the point on the needle, the needle is visualized if the point on the needle is included in the ambient reflection. As a result, the visualization performance of the needle tip is reduced compared with that in the first embodiment.

(Second Embodiment)

Subsequently, an ultrasound diagnostic device according to a second embodiment of the present disclosure will be described. Since the basic configuration is the same as that in the first embodiment, the detailed explanation thereof will be omitted and the differences will be described.

In the first embodiment, in order to generate an RF signal of one scanning line in a direction that is inclined by the angle θ, one of element reception signals that share the transmission focus is used. In the second embodiment, an example will be described in which not only each of element reception signals that share the transmission focus but also plural element reception signals including the periphery are used in order to generate the RF signal of one scanning line.

That is, in the second embodiment, the transmission unit 14 transmits ultrasound waves from plural ultrasound elements so as to transmit an ultrasound beam by forming a transmission focus in a first direction in each of two or more different openings of the probe 36. When generating reception data (acoustic ray signal) by performing reception focusing in a direction, which is inclined by the angle θ with respect to the vertical direction, using element data obtained by an element data processing unit 22, the second reception focusing section 40B performs reception focusing using the element reception signals of plural scanning lines.

Figure 8:
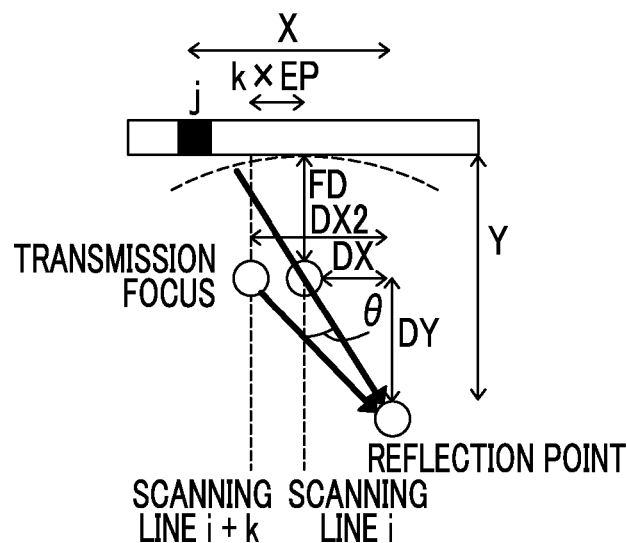
FIG. 8 is a diagram for explaining reception focusing in a θ direction using the element signals of plural scanning lines, which is performed by a second reception focusing section in an ultrasound diagnostic device according to a second embodiment of the present disclosure.

Here, reception focusing in the θ direction using the element signals of plural scanning lines will be described with reference to FIG. 8.

First, a method in which specular reflection is not assumed will be described with reference to FIG. 8.

Distances DX and DY of the reflection point in the θ direction of the scanning line i from the transmission focus are given by the following equations as described above.

$$DX = (V \times Tt - FD) \times \sin(\theta)$$

$$DY = (V \times Tt - FD) \times \cos(\theta)$$

$$Tt = T0/2$$

Then, the distance of the reflection point from the transmission focus of the scanning line (i+k) is calculated.

Since the scanning line (i+k) is spaced apart from the scanning line i by k×EP, DX2 is expressed as follows.

$$DX2 = DX - k \times EP$$

Here, k is a positive or negative value with the i-th scanning line as 0.

In addition, the distance is given as follows.

$$\operatorname{sign}(DY) \times \operatorname{sqrt}(DX2^2 + DY^2)$$

Here, when DY is negative, sign(DY) is also multiplied in order to set the distance to a negative value.

It can be seen that the time until the acoustic wave transmitted from the opening of the scanning line (i+k) reaches the reflection point is as follows.

$$Tt2 = (FD + \operatorname{sign}(DY) \times \operatorname{sqrt}(DX2^2 + DY^2))/V$$

On the other hand, it can be seen that the propagation time of the acoustic wave, which returns from the reflection point to the j-th element (has a positive or negative value with an element corresponding to the position of the scanning line (i+k) as 0) of the opening of the scanning line (i+k), is as follows.

$$Tr = \mathrm{sqrt}(X^2+Y^2)/V$$

Here, $X=DX-(k+j)\times EP$, and $Y=DY+FD$.

Therefore, by adding up the signals of the respective elements of each scanning line using the following equations, it is possible to extract the reflected wave from the reflection point, that is, it is possible to perform reception focusing.

$$RF(i, T0) = \Sigma\Sigma ELE(i+k, j, T)$$

$$T = Tt2 + Tr$$

Here, i+k indicates a scanning line, j indicates an element, one of two $\Sigma$ indicates integration on k, and the other $\Sigma$ indicates integration on j.

That is, reception focusing in the θ direction using the element signals of plural scanning lines (method in which specular reflection is not assumed) is performed so as to satisfy the following equations.

$$RF(i, T0) = \Sigma\Sigma ELE(i+k, j, T)$$

$$T = Tt2 + Tr$$

$$Tr = \mathrm{sqrt}(X^2+Y^2)/V$$

$$X = DX - (k+j) \times EP$$

$$Y = DY + FD$$

$$Tt2 = (FD + \mathrm{sign}(DY) \times \mathrm{sqrt}(DX2^2 + DY^2))/V$$

$$DX2 = DX - k \times EP$$

$$DX = (V \times Tt - FD) \times \sin(\theta)$$

$$DY = (V \times Tt - FD) \times \cos(\theta)$$

$$Tt = T0/2$$

By performing reception focusing using the element reception signals of plural scanning lines as described above, it is possible to improve the visualization of a reflector, such as a needle, other than the tissue, compared with the first embodiment.

Figure 9A:
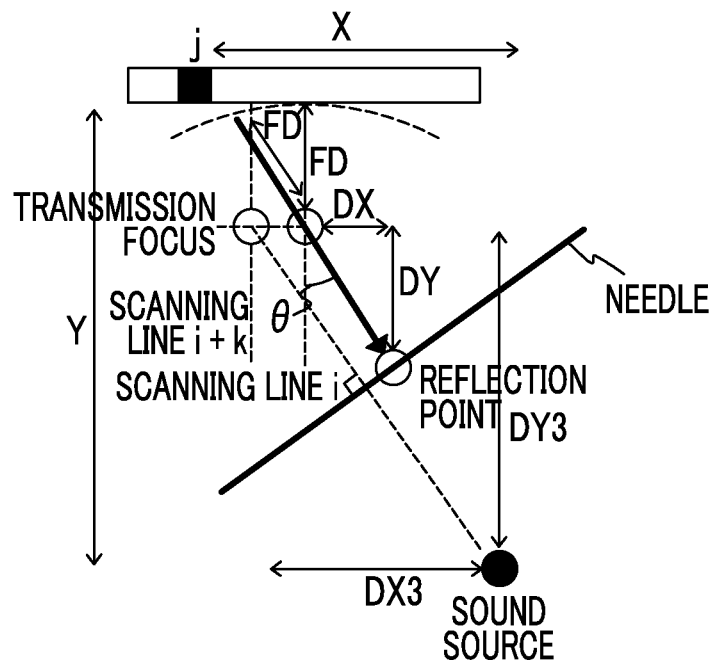
FIG. 9A is a diagram for explaining reception focusing in a θ direction using the element signals of plural scanning lines, which is performed by the second reception focusing section in the ultrasound diagnostic device according to the second embodiment of the present disclosure (when an acoustic wave equivalent to a case in which a sound source is present at the symmetrical position with the needle as a specular reflection surface is taken into consideration).

Next, a case in which reception focusing is performed in consideration of the fact that the reflected wave from the needle becomes an acoustic wave equivalent to a case in which a sound source is present at the symmetrical position with the needle as a specular reflection surface will be described with reference to FIGS. 9A and 9B.

First, distances DX and DY of the reflection point in the θ direction of the scanning line i from the transmission focus are given by the following equations as described above (FIG. 9A).

$$DX = (V \times Tt - FD) \times \sin(\theta)$$

$$DY = (V \times Tt - FD) \times \cos(\theta)$$

$$Tt = T0/2$$

Then, a pseudo sound source is assumed at the symmetrical position of the transmission focus of the scanning line i+k with respect to the needle, and distances DX3 and DY3 from the transmission focus of the scanning line i+k to the pseudo sound source are calculated.

Figure 9B:
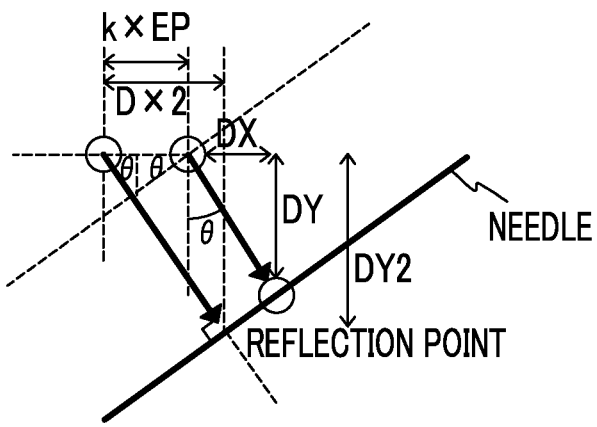
FIG. 9B is a diagram for explaining reception focusing in a θ direction using the element signals of plural scanning lines, which is performed by the second reception focusing section in the ultrasound diagnostic device according to the second embodiment of the present disclosure (when an acoustic wave equivalent to a case in which a sound source is present at the symmetrical position with the needle as a specular reflection surface is taken into consideration).

First, it can be seen that DX2 in FIG. 9B is given by the following equation (here, k is a positive or negative value with the i-th scanning line as 0).

$$DX2 = DX - k \times EP \times \sin(\theta) \times \sin(\theta)$$

In addition, it can be seen that DY2 is given by the following equation.

$$DY2 = DY - k \times EP \times \sin(\theta) \times \cos(\theta)$$

Since DX3 and DY3 are values obtained by doubling DX2 and DY2, DX3 and DY3 are expressed as follows.

$$DX3 = 2 \times DX2$$

$$DY3 = 2 \times DY2$$

If DX3 and DY3 are known, it can be seen that the propagation time of the acoustic wave, which returns from the sound source to the j-th element (has a positive or negative value with an element corresponding to the position of the scanning line (i+k) as 0) of the opening of the scanning line (i+k), is as follows.

$$Tr = \mathrm{sqrt}(X^2+Y^2)/V$$

Here, $X=DX3-j\times EP$, and $Y=DY3+FD$.

Therefore, by adding up the signals of the respective elements of each scanning line using the following equations, it is possible to extract the reflected wave from the reflection point, that is, it is possible to perform reception focusing.

$$RF(i, T0) = \Sigma\Sigma ELE(i+k, j, T)$$

$$T = FD/V + Tr$$

Here, i+k indicates a scanning line, j indicates an element, one of two $\Sigma$ indicates integration on k, and the other $\Sigma$ indicates integration on j.

That is, reception focusing in the second reception focusing section 40B is performed so as to satisfy the following equations.

$$RF(i, T0) = \Sigma\Sigma ELE(i+k, j, T)$$

$$T = FD/V + Tr$$

$$Tr = \mathrm{sqrt}(X^2+Y^2)/V$$

$$X = DX3 - j \times EP$$

$$Y = DY3 + FD$$

$$DX3 = 2 \times DX2$$

$$DY3 = 2 \times DY2$$

$$DX2 = DX - k \times EP \times \sin(\theta) \times \sin(\theta)$$

$$DY2 = DY - k \times EP \times \sin(\theta) \times \cos(\theta)$$

$$DX = (V \times Tt - FD) \times \sin(\theta)$$

$$DY = (V \times Tt - FD) \times \cos(\theta)$$

$$Tt = T0/2$$

Subsequently, the operation of the ultrasound diagnostic device according to the second embodiment of the present disclosure and a method of generating an ultrasound image will be described.

FIG. 10 is a flowchart showing an example of the flow of the process performed by the main part of the ultrasound diagnostic device 10 according to the second embodiment of the present disclosure.

In step 200, a scanning line n is reset (n=0), and the process proceeds to step 202. In step 202, the scanning line n is incremented by 1 (n=n+1), and the process proceeds to step 204.

In step 204, transmission focusing is performed to acquire each element reception signal, and the process proceeds to step 206. That is, when the operator brings the ultrasound probe 12 into contact with the surface of the subject to start measurement, an ultrasound beam is transmitted from the probe 36 according to the driving signal supplied from the transmission unit 14. Then, the ultrasound echo generated by interaction between the transmitted ultrasound beam and the subject is received by the probe 36, the analog element signal is amplified by the receiving unit 16, the amplified analog element signal is converted into digital element data by the A/D conversion unit 18, and the digital element data is stored in the element data storage unit 20.

In step 206, it is determined whether or not n=N. That is, it is determined whether or not the above processing has ended for all the scanning lines. When the determination is negative, the process returns to step 202 to repeat the above processing. When the determination is positive, the process proceeds to step 208.

In step 208, a scanning line n is reset (n=0), and the process proceeds to step 210. In step 210, the scanning line n is incremented by 1 (n=n+1), and the process proceeds to step 212.

In step 212, the image A for tissue imaging is generated by performing reception focusing in the same direction as the transmission beam for each element reception signal, and the process proceeds to step 214. That is, the first reception focusing section 40A acquires each element reception signal from the element data storage unit 20 and generates reception data (acoustic ray signal) by performing reception focusing in the vertical direction, and the first detection processing section 40C generates a B-mode image signal of the image A for tissue imaging by processing the acoustic ray signal.

In step 214, the image B for needle imaging is generated by performing reception focusing in a direction, which is inclined by the angle θ with respect to the transmission beam, for each element reception signal, and the process proceeds to step 216. That is, the second reception focusing section 40B acquires each element reception signal from the element data storage unit 20 and generates reception data (acoustic ray signal) by performing reception focusing in a direction that is inclined by the angle θ with respect to the vertical direction, and the second detection processing section 40D generates a B-mode image signal of the image B for needle imaging by processing the acoustic ray signal.

In step 216, it is determined whether or not n=N. That is, it is determined whether or not the above processing has ended for all the scanning lines. When the determination is negative, the process returns to step 210 to repeat the above processing. When the determination is positive, the process proceeds to step 218.

In step 218, the combination processing section 40E generates a display image of one frame by combining the image A and the image B, which have been generated as described above, by scan conversion, and the series of processes are ended. A display image of the next frame is generated by performing the process from the processing of step 200.

By performing such processing, reception focusing using the element reception signals of plural scanning lines becomes possible. Therefore, it is possible to improve the performance of visualizing a reflector, such as a needle, other than the tissue, compared with the first embodiment.

(Third Embodiment)

Subsequently, an ultrasound diagnostic device according to a third embodiment of the present disclosure will be described.

The reflection wave from the needle becomes an acoustic wave equivalent to a case in which a sound source is present at the symmetrical position with the needle as a specular reflection surface. However, since the range is determined and limited by the transmission opening, depth, frequency, and the like, the needle may not be able to be visualized in each of the embodiments described above in the case of an acute angle.

Therefore, in the present embodiment, the transmission beam direction is inclined so as to be almost perpendicular to the needle, and then the transmission beam is further inclined to perform reception focusing.

The basic configuration is the same as those in the first and second embodiments, and only the processes are different. Accordingly, only the differences will be described.

In the ultrasound diagnostic device according to the third embodiment, the transmission beam is inclined. Accordingly, reception focusing by the second reception focusing section 40B is performed as follows.

Figure 11:
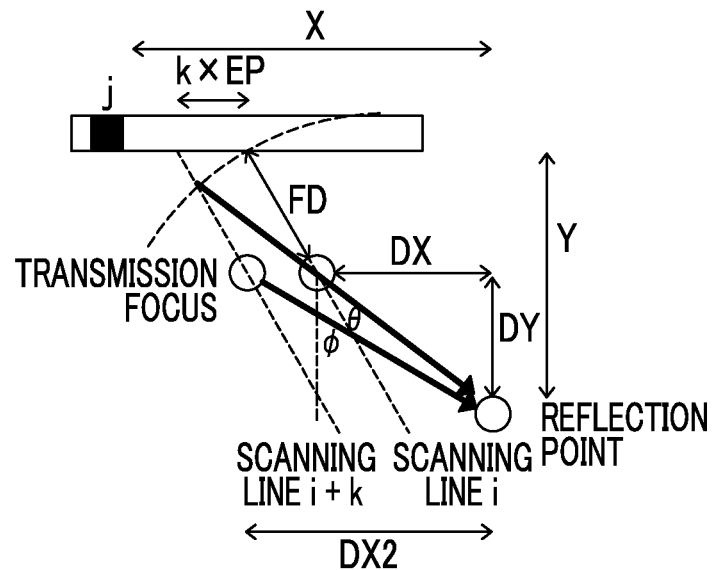
FIG. 11 is a diagram for explaining reception focusing performed by a second reception focusing section in an ultrasound diagnostic device according to a third embodiment of the present disclosure.

First, a case in which specular reflection is not assumed will be described with reference to FIG. 11.

Assuming that the scanning line i is inclined by the angle $\phi$, distances DX and DY of the reflection point in a direction, which is further inclined by the angle θ, from the transmission focus are given by the following equations.

$$DX=(V \times Tt-FD) \times \sin(\phi+\theta)$$

$$DY=(V \times Tt-FD) \times \cos(\phi+\theta)$$

$$Tt=T0/2$$

Then, the distance of the reflection point from the transmission focus of the scanning line (i+k) is calculated.

Since the scanning line (i+k) is spaced apart from the scanning line i by k×EP, DX2 is expressed as follows.

$$DX2=DX-k \times EP$$

In addition, the distance is given as follows.

$$\text{sign}(DY) \times \sqrt{DX2^2+DY^2}$$

Here, when DY is negative, sign(DY) is also multiplied in order to set the distance to a negative value.

It can be seen that the time until the acoustic wave transmitted from the opening of the scanning line (i+k) reaches the reflection point is as follows.

$$Tt2=(FD+\text{sign}(DY) \times \sqrt{DX2^2+DY^2})/V$$

On the other hand, it can be seen that the propagation time of the acoustic wave, which returns from the reflection point to the j-th element (has a positive or negative value with an element corresponding to the position of the scanning line (i+k) as 0) of the opening of the scanning line (i+k), is as follows.

$$Tr=\sqrt{X^2+Y^2}/V$$

Here, X=DX+FD×sin($\phi$)−(k+j)×EP, and Y=DY+FD×cos($\phi$).

Therefore, by adding up the signals of the respective elements of each scanning line using the following equations, it is possible to extract the reflected wave from the reflection point, that is, it is possible to perform reception focusing.

$$RF(i, T0) = \Sigma\Sigma ELE(i+k, j, T)$$

$$T = Tt2 + Tr$$

Here, i+k indicates a scanning line, j indicates an element, one of two Σ indicates integration on k, and the other Σ indicates integration on j.

That is, when performing reception focusing in a direction that is further inclined by the angle θ with respect to the transmission beam inclined by the angle φ, reception focusing by the second reception focusing section 40B is performed so as to satisfy the following equations.

$$RF(i, T0) = \Sigma\Sigma ELE(i+k, j, T)$$

$$T = Tt2 + Tr$$

$$Tr = \mathrm{sqrt}(X^2 + Y^2)/V$$

$$X = DX + FD \times \sin(\phi) - (k+j) \times EP$$

$$Y = DY + FD \times \cos(\phi)$$

$$Tt2 = (FD + \mathrm{sign}(DY) \times \mathrm{sqrt}(DX2^2 + DY^2))/V$$

$$DX2 = DX - k \times EP$$

$$DX = (V \times Tt - FD) \times \sin(\phi + \theta)$$

$$DY = (V \times Tt - FD) \times \cos(\phi + \theta)$$

$$Tt = T0/2$$

In addition, if integration on k is not performed, one of element reception signals that share the transmission focus is used.

Next, a case in which reception focusing is performed in consideration of the fact that the reflected wave from the needle becomes an acoustic wave equivalent to a case in which a sound source is present at the symmetrical position with the needle as a specular reflection surface will be described with reference to FIGS. 12A and 12B.

Figure 12A:
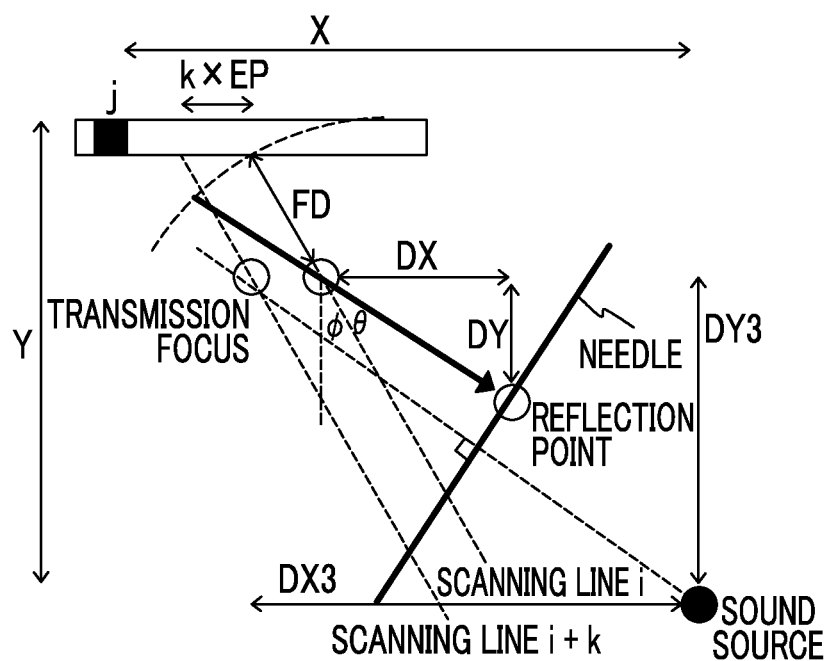
FIG. 12A is a diagram for explaining reception focusing performed by the second reception focusing section in the ultrasound diagnostic device according to the third embodiment of the present disclosure (when an acoustic wave equivalent to a case in which a sound source is present at the symmetrical position with the needle as a specular reflection surface is taken into consideration).

Assuming that the scanning line i is inclined by the angle φ, distances DX and DY of the reflection point in a direction, which is further inclined by the angle θ, from the transmission focus are given by the following equations (FIG. 12A).

$$DX = (V \times Tt - FD) \times \sin(\phi + \theta)$$

$$DY = (V \times Tt - FD) \times \cos(\phi + \theta)$$

$$Tt = T0/2$$

Then, a pseudo sound source is assumed at the symmetrical position of the transmission focus of the scanning line i+k with respect to the needle, and distances DX3 and DY3 from the transmission focus of the scanning line i+k to the pseudo sound source are calculated.

Figure 12B:
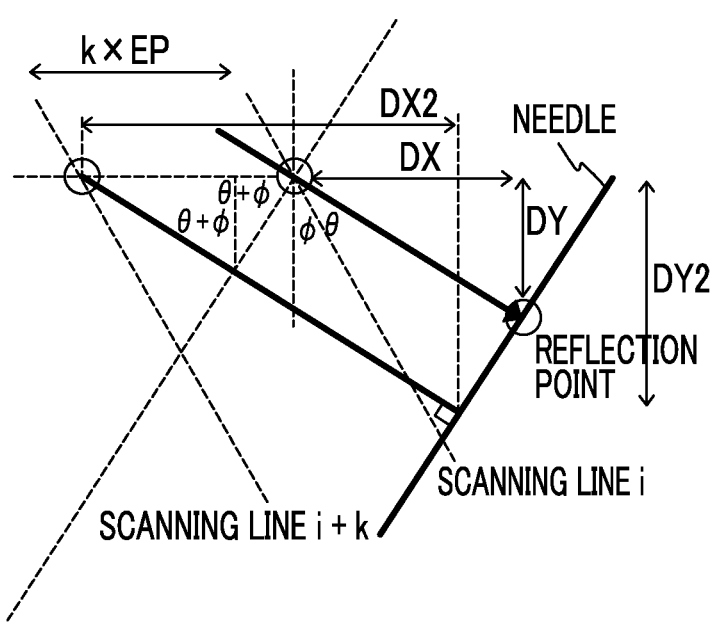
FIG. 12B is a diagram for explaining reception focusing performed by the second reception focusing section in the ultrasound diagnostic device according to the third embodiment of the present disclosure (when an acoustic wave equivalent to a case in which a sound source is present at the symmetrical position with the needle as a specular reflection surface is taken into consideration).

For the above, first, DX2 and DY2 are calculated in FIG. 12B. It can be seen that DX2 and DY2 are given by the following equations (here, k is a positive or negative value with the i-th scanning line as 0).

$$DX2 = DX - k \times EP \times \sin(\phi + \theta) \times \sin(\phi + \theta)$$

$$DY2 = DY - k \times EP \times \sin(\phi + \theta) \times \cos(\phi + \theta)$$

Since DX3 and DY3 are values obtained by doubling DX2 and DY2, DX3 and DY3 are expressed as follows.

$$DX3 = 2 \times DX2$$

$$DY3 = 2 \times DY2$$

If DX3 and DY3 are known, it can be seen that the propagation time of the acoustic wave, which returns from the sound source to the j-th element (has a positive or negative value with an element corresponding to the position of the scanning line (i+k) as 0) of the opening of the scanning line (i+k), is as follows.

$$Tr = \mathrm{sqrt}(X^2 + Y^2)/V$$

Here, $X = DX3 + FD \times \sin(\phi) - j \times EP$, and $Y = DY3 + FD \times \cos(\phi)$.

Therefore, by adding up the signals of the respective elements of each scanning line using the following equations, it is possible to extract the reflected wave from the reflection point, that is, it is possible to perform reception focusing.

$$RF(i, T0) = \Sigma\Sigma ELE(i+k, j, T)$$

$$T = FD/V + Tr$$

Here, i+k indicates a scanning line, j indicates an element, one of two Σ indicates integration on k, and the other Σ indicates integration on j.

That is, when performing reception focusing in a direction, which is further inclined by the angle θ with respect to the transmission beam inclined by the angle φ, in consideration of the fact that the reflected wave from the needle becomes an acoustic wave equivalent to a case in which a sound source is present at the symmetrical position with the needle as a specular reflection surface, the second reception focusing section 40B performs reception focusing so as to satisfy the following equations.

$$RF(i, T0) = \Sigma\Sigma ELE(i+k, j, T)$$

$$T = FD/V + Tr$$

$$Tr = \mathrm{sqrt}(X^2 + Y^2)/V$$

$$X = DX3 + FD \times \sin(\phi) - j \times EP$$

$$Y = DY3 + FD \times \cos(\phi)$$

$$DX3 = 2 \times DX2$$

$$DY3 = 2 \times DY2$$

$$DX2 = DX - k \times EP \times \sin(\phi + \theta) \times \sin(\phi + \theta)$$

$$DY2 = DY - k \times EP \times \sin(\phi + \theta) \times \cos(\phi + \theta)$$

$$DX = (V \times Tt - FD) \times \sin(\phi + \theta)$$

$$DY = (V \times Tt - FD) \times \cos(\phi + \theta)$$

$$Tt = T0/2$$

In addition, if integration on k is not performed, one of element reception signals that share the transmission focus is used.

FIG. 13 is a flowchart showing an example of the flow of the process performed by the main part of the ultrasound diagnostic device according to the third embodiment of the present disclosure. The same processing as in the second embodiment will be described using the same reference numerals.

In step 200, a scanning line n is reset (n=0), and the process proceeds to step 202. In step 202, the scanning line n is incremented by 1 (n=n+1), and the process proceeds to step 203.

In step 203, transmission focusing is performed without tilting the transmission beam to acquire each element reception signal, and the process proceeds to step 205. That is, when the operator brings the ultrasound probe 12 into contact with the surface of the subject to start measurement, an ultrasound beam is transmitted from the probe 36 according to the driving signal supplied from the transmission unit 14. Then, the ultrasound echo generated by interaction between the transmitted ultrasound beam and the subject is received by the probe 36, the analog element signal is amplified by the receiving unit 16, the amplified analog element signal is converted into digital element data by the A/D conversion unit 18, and the digital element data is stored in the element data storage unit 20.

In step 205, transmission focusing is performed by tilting the transmission beam to acquire each element reception signal, and the process proceeds to step 206. That is, according to the driving signal supplied from the transmission unit 14, an ultrasound beam is transmitted from the probe 36. In this case, unlike in step 203, the transmission beam is transmitted so as to be inclined. Then, the ultrasound echo generated by interaction between the transmitted ultrasound beam and the subject is received by the probe 36, the analog element signal is amplified by the receiving unit 16, the amplified analog element signal is converted into digital element data by the A/D conversion unit 18, and the digital element data is stored in the element data storage unit 20.

In step 206, it is determined whether or not n=N. That is, it is determined whether or not the above processing has ended for all the scanning lines. When the determination is negative, the process returns to step 202 to repeat the above processing. When the determination is positive, the process proceeds to step 208.

In step 208, a scanning line n is reset (n=0), and the process proceeds to step 210. In step 210, the scanning line n is incremented by 1 (n=n+1), and the process proceeds to step 213.

In step 213, the image A for tissue imaging is generated by performing reception focusing in the same direction as the transmission beam for each element reception signal acquired without tilting the transmission beam, and the process proceeds to step 215. That is, the first reception focusing section 40A acquires each element reception signal acquired in step 203 from the element data storage unit 20 and generates reception data (acoustic ray signal) by performing reception focusing in the vertical direction, and the first detection processing section 40C generates a B-mode image signal of the image A for tissue imaging by processing the acoustic ray signal.

In step 215, the image B for needle imaging is generated by performing reception focusing in a direction, which is inclined by the angle θ with respect to the transmission beam, for each element reception signal acquired by tilting the transmission beam, and the process proceeds to step 216. That is, the second reception focusing section 40B acquires each element reception signal acquired in step 205 from the element data storage unit 20 and generates reception data (acoustic ray signal) by performing reception focusing in a direction that is further inclined by the angle θ with respect to the transmission beam, and the second detection processing section 40D generates a B-mode image signal of the image B for needle imaging by processing the acoustic ray signal.

In step 216, it is determined whether or not n=N. That is, it is determined whether or not the above processing has ended for all the scanning lines. When the determination is negative, the process returns to step 210 to repeat the above processing. When the determination is positive, the process proceeds to step 218.

In step 218, the combination processing section 40E generates a display image of one frame by combining the image A and the image B, which have been generated as described above, by scan conversion, and the series of processes are ended. A display image of the next frame is generated by performing the process from the processing of step 200.

In FIG. 13, the case has been described in which the RF signal of one scanning line is generated using the element reception signals of plural scanning lines. However, when one of the element reception signals that share the transmission focus is used in order to generate the RF signal of one scanning line as in the first embodiment, processing shown in FIG. 14 may be performed instead of FIG. 13.

Figure 14:
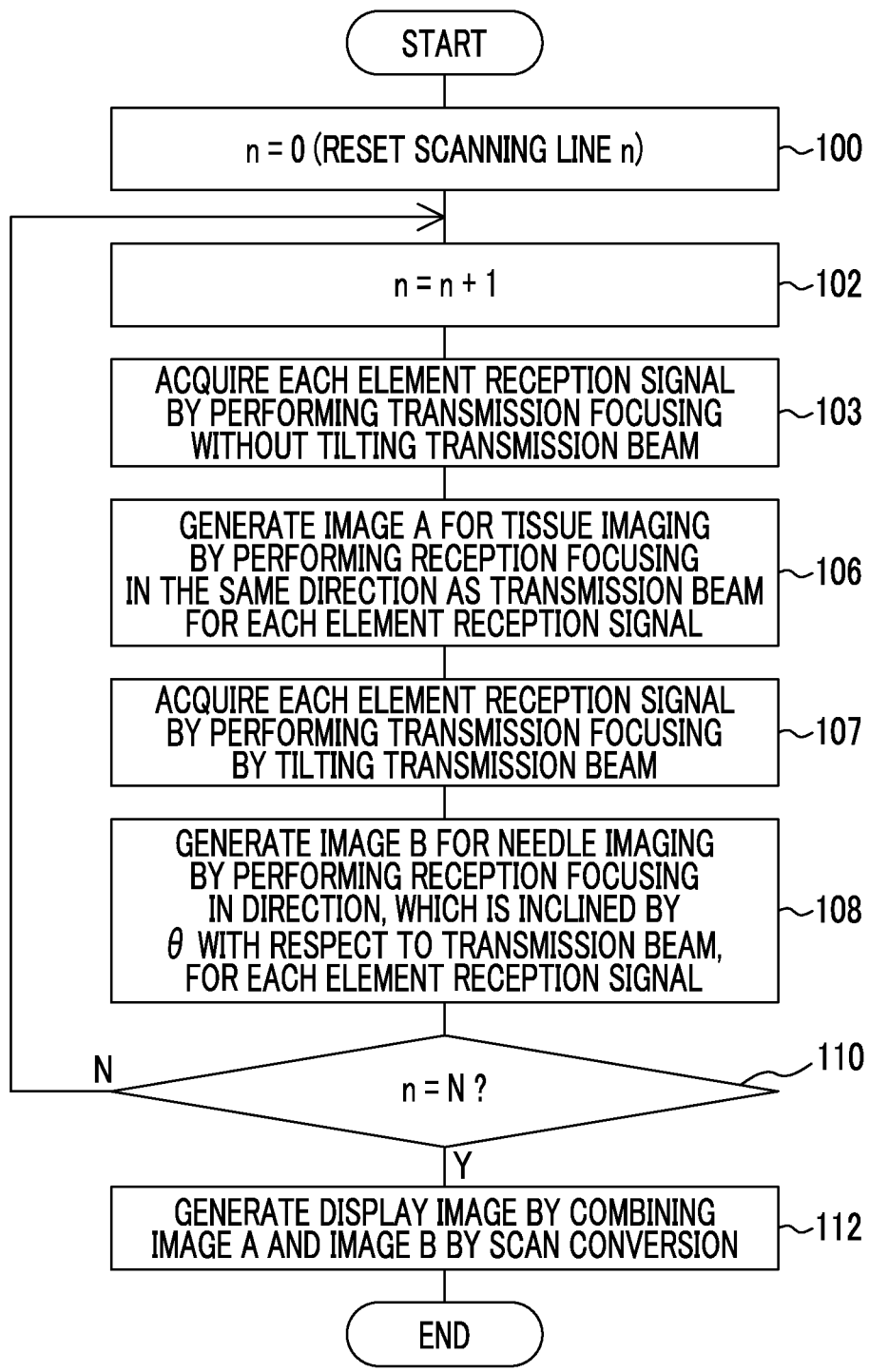
FIG. 14 is a flowchart showing an example of the flow of the process when generating the RF signal of one scanning line using one of element reception signals that share the transmission focus in the ultrasound diagnostic device according to the third embodiment of the present disclosure.

FIG. 14 is a flowchart showing an example of the flow of the process when generating the RF signal of one scanning line using one of the element reception signals that share the transmission focus in the ultrasound diagnostic device according to the third embodiment of the present disclosure. The same processing as in the first embodiment will be described using the same reference numerals.

In step 100, a scanning line n is reset (n=0), and the process proceeds to step 102. In step 102, the scanning line n is incremented by 1 (n=n+1), and the process proceeds to step 103.

In step 103, transmission focusing is performed in the vertical direction without tilting the transmission beam to acquire each element reception signal, and the process proceeds to step 106. That is, when the operator brings the ultrasound probe 12 into contact with the surface of the subject to start measurement, an ultrasound beam is transmitted from the probe 36 according to the driving signal supplied from the transmission unit 14. Then, the ultrasound echo generated by interaction between the transmitted ultrasound beam and the subject is received by the probe 36, the analog element signal is amplified by the receiving unit 16, the amplified analog element signal is converted into digital element data by the A/D conversion unit 18, and the digital conversion element data is stored in the element data storage unit 20.

In step 106, the image A for tissue imaging is generated by performing reception focusing in the same direction as the transmission beam for the reception signal of each element, and the process proceeds to step 107. That is, the first reception focusing section 40A acquires each element reception signal from the element data storage unit 20 and generates reception data (acoustic ray signal) by performing reception focusing in the vertical direction, and the first detection processing section 40C generates a B-mode image signal of the image A for tissue imaging by processing the acoustic ray signal.

In step 107, transmission focusing is performed by tilting the transmission beam to acquire each element reception signal, and the process proceeds to step 108. That is, according to the driving signal supplied from the transmission unit 14, an ultrasound beam is transmitted from the probe 36. In this case, unlike in step 103, the transmission beam is transmitted so as to be inclined. Then, the ultrasound echo generated by interaction between the transmitted ultrasound beam and the subject is received by the probe 36, the analog element signal is amplified by the receiving unit 16, the amplified analog element signal is converted into digital element data by the A/D conversion unit 18, and the digital element data is stored in the element data storage unit 20.

In step 108, the image B for needle imaging is generated by performing reception focusing in a direction, which is inclined by the angle θ with respect to the transmission beam (inclined transmission beam), for the reception signal of each element, and the process proceeds to step 110. That is, the second reception focusing section 40B acquires each element reception signal obtained by the inclined transmission beam from the element data storage unit 20 and generates reception data (acoustic ray signal) by performing reception focusing in a direction that is further inclined by the angle θ with respect to the transmission beam, and the second detection processing section 40D generates a B-mode image signal of the image B for needle imaging by processing the acoustic ray signal.

In step 110, it is determined whether or not n=N. That is, it is determined whether or not the above processing has ended for all the scanning lines. When the determination is negative, the process proceeds to step 102 to repeat the above processing. When the determination is positive, the process proceeds to step 112.

In step 112, the combination processing section 40E generates a display image of one frame by combining the image A and the image B, which have been generated as described above, by scan conversion, and the series of processes are ended. A display image of the next frame is generated by performing the process from the processing of step 100.

Thus, the ultrasound diagnostic device according to the third embodiment of the present disclosure requires two ultrasound transmissions unlike in each of the embodiments described above. Accordingly, it is possible to reliably visualize a reflector, such as a needle at an angle that cannot be visualized in each of the embodiments described above, other than the tissue. Therefore, since a reflector, such as a needle, can be reliably visualized, it is possible to compensate for the disadvantages of the embodiments described above by performing mode switching or the like when a reflector, such as a needle, other than the tissue cannot be detected in the embodiments described above.

(Fourth Embodiment)

Subsequently, an ultrasound diagnostic device according to a fourth embodiment will be described.

In the fourth embodiment, reception focusing by the second reception focusing section 40B when using a convex type ultrasound probe in the third embodiment will be described.

The reception focusing of the second reception focusing section 40B when transmitting the transmission beam, which is inclined by the angle φ, using the convex type ultrasound probe will be described.

First, a case in which specular reflection is not assumed will be described with reference to FIGS. 15A and 15B.

Figure 15A:
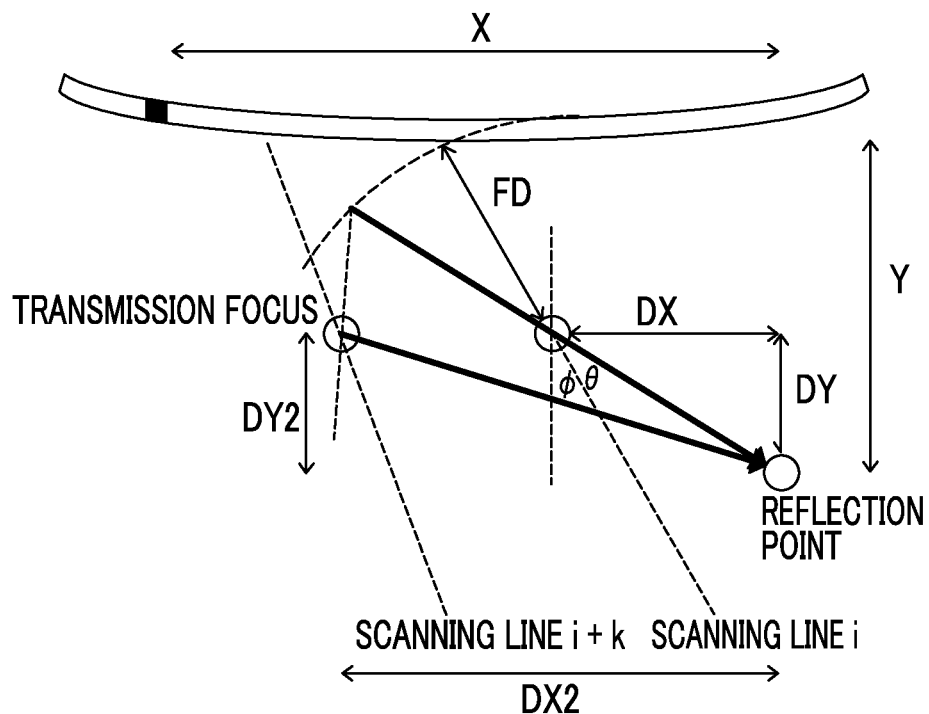
FIG. 15A is a diagram for explaining reception focusing performed by the second reception focusing section in the ultrasound diagnostic device according to the third embodiment of the present disclosure.

Assuming that the scanning line i is inclined by the angle φ, X-direction and Y-direction distances DX and DY of the reflection point in a direction, which is further inclined by the angle θ, from the transmission focus are given by the following equations (FIG. 15A).

$$DX=(V \times Tt-FD) \times \sin(\phi+\theta)$$

$$DY=(V \times Tt-FD) \times \cos(\phi+\theta)$$

$$Tt=T0/2$$

Then, the X-direction and Y-direction distances of the reflection point from the transmission focus of the scanning line (i +k) are calculated.

Figure 15B:
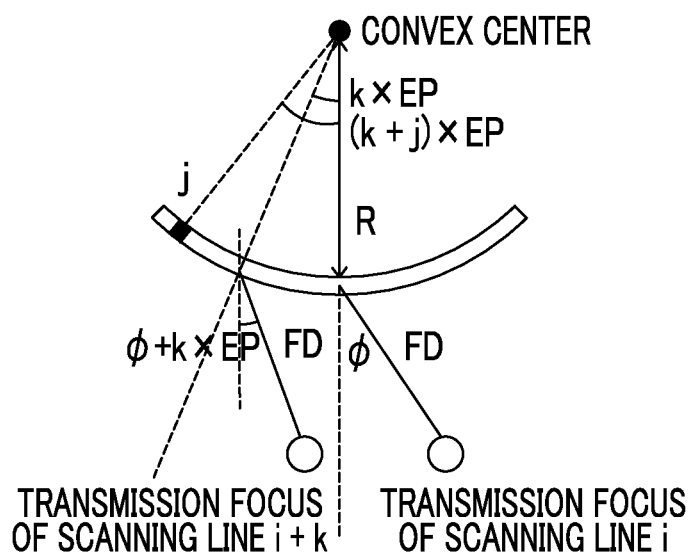
FIG. 15B is a diagram for explaining reception focusing performed by the second reception focusing section in the ultrasound diagnostic device according to the third embodiment of the present disclosure.

First, the X-direction and Y-direction distances of the transmission focus of the scanning line i with respect to the transmission focus of the scanning line (i+k) are calculated from FIG. 15B. The x and y coordinates of the transmission focus of the scanning line i with the convex center as the origin are as follows.

$$x_i=FD \times \sin(\phi)$$

$$y_i=R+FD \times \cos(\phi)$$

Here, R indicates the radius of the convex type ultrasound probe.

The scanning line (i+k) is inclined by the angle k×EP with respect to the scanning line i. Accordingly, it can be seen from FIG. 15B that the scanning line i is inclined by the angle φ with respect to the y direction while the scanning line (i+k) is inclined by φ+k×EP with respect to the y direction (here, EP is an angle between the scanning lines, and k is a positive or negative value with the i-th scanning line as 0). Therefore, the x and y coordinates of the transmission focus of the scanning line (i+k) are expressed as follows.

$$x_{i+k}=R \times \sin(k \times EP)+FD \times \sin(\phi+k \times EP)$$

$$y_{i+k}=R \times \cos(k \times EP)+FD \times \cos(\phi+k \times EP)$$

Based on the above equations, the X-direction and Y-direction distances of the transmission focus of the scanning line i with respect to the transmission focus of the scanning line (i+k) are calculated by the following equations.

$$x_i-x_{i+k}=FD \times \sin(\phi)-R \times \sin(k \times EP)-FD \times \sin(\phi+k \times EP)$$

$$y_i-y_{i+k}=R+FD \times \cos(\phi)-R \times \cos(k \times EP)-FD \times \cos(\phi+k \times EP)$$

Therefore, the X-direction distance DX2 and Y-direction distance DY2 of the reflection point with respect to the transmission focus of the scanning line (i+k) are calculated by the following equations.

$$DX2=DX+FD \times \sin(\phi)-FD \times \sin(\phi+k \times EP)-R \times \sin(k \times EP)$$

$$DY2=DY+FD \times \cos(\phi)-FD \times \cos(\phi+k \times EP)+R-R \times \cos(k \times EP).$$

It can be seen that the time until the acoustic wave transmitted from the opening of the scanning line (i+k) reaches the reflection point is as follows.

$$Tt2=(FD+\text{sign}(DY) \times \text{sqrt}(DX2^2+DY2^2))/V.$$

Here, when DY is negative, the acoustic wave reaches the reflection point before forming the transmission focus. Accordingly, sign(DY) is multiplied.

On the other hand, from FIG. 15B, it can be seen that the propagation time of the acoustic wave, which returns from the reflection point to the j-th element (has a positive or negative value with an element corresponding to the position of the scanning line (i+k) as 0) of the opening of the scanning line (i+k), is as follows.

$$Tr=\text{sqrt}(X^2+Y^2)/V$$

Here, X=DX+FD×sin(φ)−R×sin((k+j)×EP), and Y=DY+FD×cos(φ)+R−R×cos((k+j)×EP).

Here, EP is an angle between the scanning lines and is also an angle between elements.

Therefore, by adding up the signals of the respective elements of each scanning line using the following equations, it is possible to extract the reflected wave from the reflection point, that is, it is possible to perform reception focusing.

$$RF(i, T0)=\Sigma\Sigma ELE(i+k, j, T)$$

$$T=Tt2+Tr$$

Here, i+k indicates a scanning line, j indicates an element, one of two Σ indicates integration on k, and the other Σ indicates integration on j.

That is, when transmitting the transmission beam that is inclined by the angle φ using the convex type ultrasound probe, reception focusing in a direction that is further inclined by the angle θ is performed so as to satisfy the following equations.

$$RF(i, T0) = \Sigma\Sigma ELE(i+k, j, T)$$

$$T = Tt2 + Tr$$

$$Tr = \text{sqrt}(X^2 + Y^2)/V$$

$$X = DX + FD \times \sin(\phi) - R \times \sin((k+j) \times EP)$$

$$Y = DY + FD \times \cos(\phi) + R - R \times \cos((k+j) \times EP)$$

$$Tt2 = (FD + \text{sign}(DY) \times \text{sqrt}(DX2^2 + DY2^2))/V$$

$$DX2 = DX + FD \times \sin(\phi) - FD \times \sin(\phi + k \times EP) - R \times \sin(k \times EP)$$

$$DY2 = DY + FD \times \cos(\phi) - FD \times \cos(\phi + k \times EP) + R - R \times \cos(k \times EP)$$

$$DX = (V \times Tt - FD) \times \sin(\phi + \theta)$$

$$DY = (V \times Tt - FD) \times \cos(\phi + \theta)$$

$$Tt = T0/2$$

Figure 16:
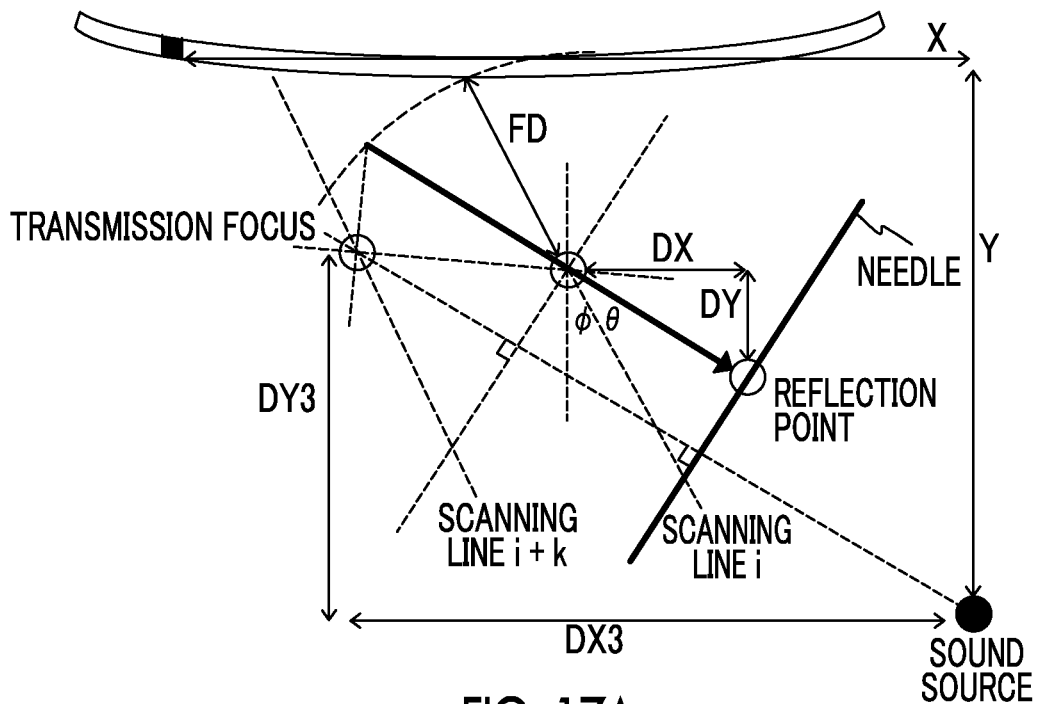
FIG. 16 is a diagram for explaining reception focusing performed by the second reception focusing section in the ultrasound diagnostic device according to the third embodiment of the present disclosure (when an acoustic wave equivalent to a case in which a sound source is present at the symmetrical position with the needle as a specular reflection surface is taken into consideration).

Next, a case in which reception focusing is performed in consideration of the fact that the reflected wave from the needle becomes an acoustic wave equivalent to a case in which a sound source is present at the symmetrical position with the needle as a specular reflection surface will be described with reference to FIGS. 16, 17A, and 17B.

Assuming that the scanning line i is inclined by the angle φ, distances DX and DY of the reflection point in a direction, which is further inclined by the angle θ, from the transmission focus are given by the following equations.

$$DX = (V \times Tt - FD) \times \sin(\phi + \theta)$$

$$DY = (V \times Tt - FD) \times \cos(\phi + \theta)$$

$$Tt = T0/2$$

Then, a pseudo sound source is assumed at the symmetrical position of the transmission focus of the scanning line i+k with respect to the needle, and distances DX3 and DY3 from the transmission focus of the scanning line i+k to the pseudo sound source are calculated.

Figure 17A:
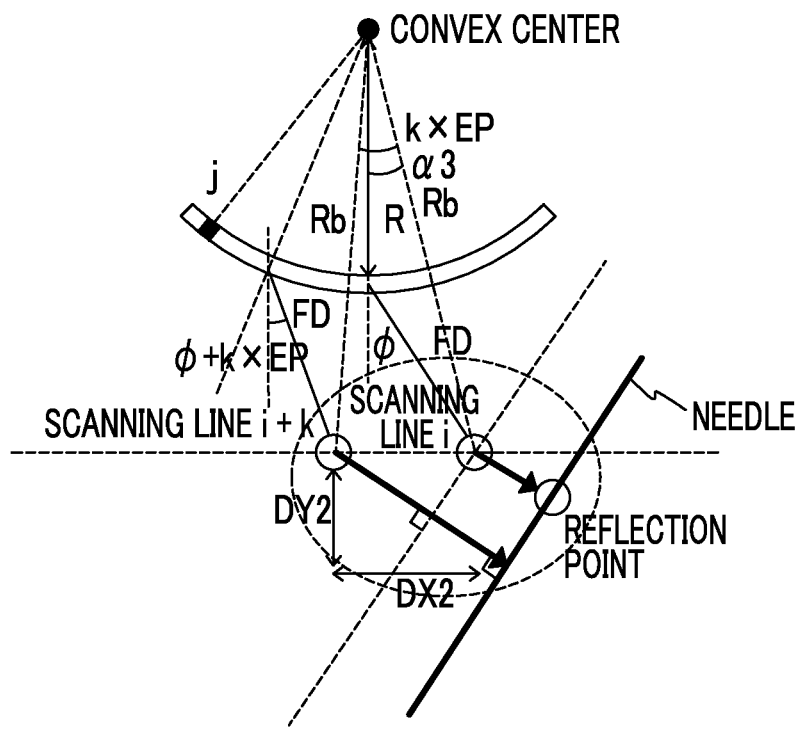
FIG. 17A is a diagram for explaining a method of calculating DX2 and DY2 in FIG. 16.
Figure 17B:
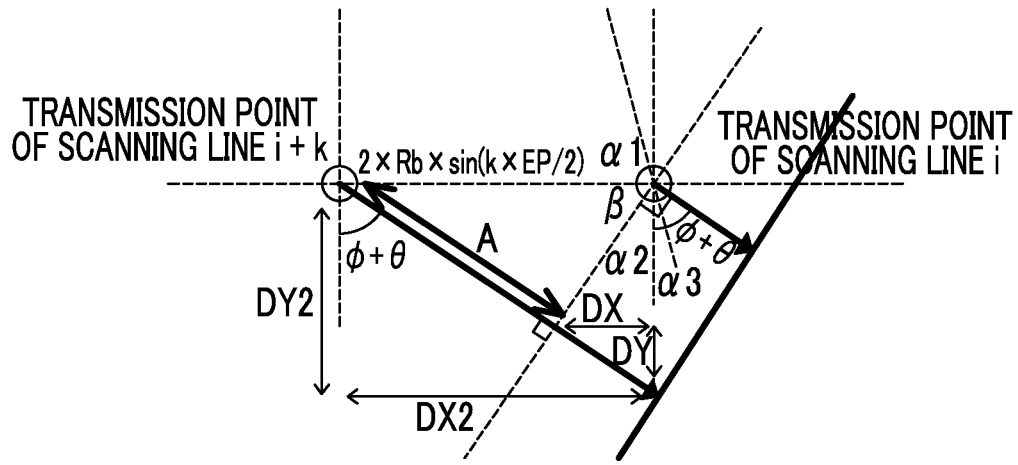
FIG. 17B is a diagram for explaining a method of calculating DX2 and DY2 in FIG. 16.
Figure 18A:
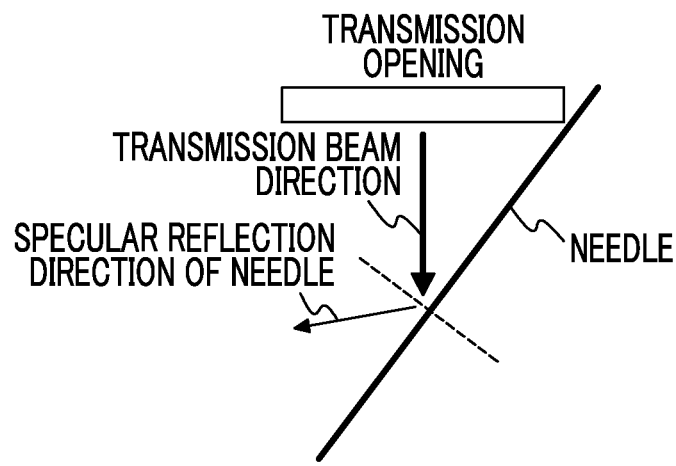
FIG. 18A is a diagram showing a state in which the reflection of the needle deviates from the reception opening.
Figure 18B:
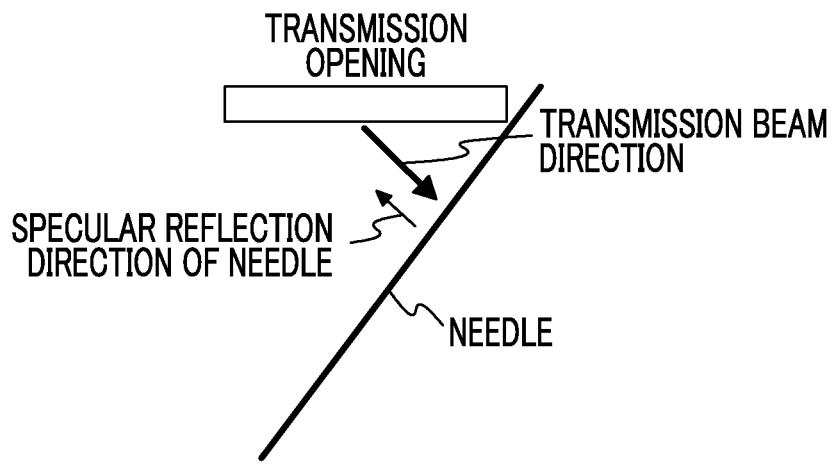
FIG. 18B is a diagram showing an example of receiving the reflection by the needle by transmitting the transmission beam so as to be inclined.

For the above, first, DX2 and DY2 are calculated in FIG. 17A (or FIG. 17B). Here, FIGS. 17A and 17B are diagrams for explaining the method of calculating DX2 and DY2, and FIG. 17B is an enlarged view of a portion surrounded by the dotted line in FIG. 17A.

In order to calculate DX2 and DY2, first, the distance of the arrow A in FIG. 17B is calculated. For the above, first, the distance between the transmission focus of the scanning line i+k and the transmission focus of the scanning line i and an angle β in FIG. 17B are calculated.

For the distance between the transmission focus of the scanning line i+k and the transmission focus of the scanning line i, referring to FIG. 17A, it can be seen that the triangle formed by the convex center and the transmission focuses is an isosceles triangle having the convex center as its apex. Assuming that the length of the side is Rb, it can be seen that Rb is given by the following equation by the cosine theorem.

$$Rb = \text{sqrt}(R^2 + FD^2 + 2 \times R \times FD \times \cos(\phi))$$

In addition, from the fact that the angle of the apex (convex center) of the isosceles triangle is k×EP, it can be seen that the distance between the transmission focus of the scanning line i+k and the transmission focus of the scanning line i is given by the following equation.

$$2 \times Rb \times \sin(k \times EP/2)$$

Then, in order to calculate β in FIG. 17B, α1, α2, and α3 are calculated first.

Since α1 is the base angle of the isosceles triangle described above, it can be seen that α1 is 90°−(k×EP/2).

From FIG. 17B, it can easily be seen that α2 is 90°−φ−θ.

It can be seen that α3 is equal to α3 in FIG. 17A. In addition, it can be seen that α3 in FIG. 17A is given by the following equation since Rb/sin(180°−φ)=FD/sin(α3) is satisfied by the sine theorem.

$$\alpha 3 = \arcsin(\sin(\phi) \times FD/Rb)$$

From above, it can be seen that β is given by the following equation.

$$\beta = 180° - \alpha 1 - \alpha 2 - \alpha 3$$
$$= (k \times EP/2) + \phi + \theta - \arcsin(\sin(\phi) \times FD/Rb)$$

From above, it can be seen that the distance of the arrow A in FIG. 17B is calculated by the following equation.

$$2 \times Rb \times \sin(k \times EP/2) \times \sin(\beta)$$

From above, DX2 and DY2 are given by the following equations.

$$DX2 = 2 \times Rb \times \sin(k \times EP/2) \times \sin(\beta) \times \sin(\phi + \theta) + DX$$

$$DY2 = 2 \times Rb \times \sin(k \times EP/2) \times \cos(\beta) \times \sin(\phi + \Theta) + DY$$

Here, $\beta = (k \times EP/2) + \phi + \theta - \arcsin(\sin(\phi) \times FD/Rb)$, and $Rb = \text{sqrt}(R^2 + FD^2 + 2 \times R \times FD \times \cos(\phi))$.

Since DX3 and DY3 are values obtained by doubling DX2 and DY2, DX3 and DY3 are expressed as follows.

$$DX3 = 2 \times DX2$$

$$DY3 = 2 \times DY2$$

The scanning line (i+k) is inclined by the angle k×EP with respect to the scanning line i. Accordingly, it can be seen from FIG. 17A that the scanning line i is inclined by the angle φ with respect to the y direction, while the scanning line (i+k) is inclined by φ+k×EP with respect to the y direction (here, k is a positive or negative value with the i-th scanning line as 0).

Therefore, the X-direction and Y-direction distances of the transmission focus to the origin of the scanning line (i+k) (center of the opening) are expressed as follows.

$$FD \times \sin(\phi + k \times EP)$$

$$FD \times \cos(\phi + k \times EP)$$

In addition, it can also be seen from FIG. 17A that the X-direction and Y-direction distances of the origin of the scanning line (i+k) (center of the opening) to the j-th element of the opening of the scanning line (i+k) are as follows.

$$R \times (\sin(k \times EP) - \sin((k+j) \times EP))$$

$$R \times (\cos(k \times EP) - \cos((k+j) \times EP))$$

From above, it can be seen that the propagation time of the acoustic wave returning to the j-th element of the opening of the scanning line (i+k) from the sound source is as follows.

$$Tr=\text{sqrt}(X^2+Y^2)/V$$

Here, X=DX3+FD×sin(φ+k×EP)+R×(sin(k×EP)−sin((k+j)×EP)), and Y=DY3+FD×cos(φ+k×EP)+R×(cos(k×EP)−cos((k+j)×EP)).

Therefore, by adding up the signals of the respective elements of each scanning line using the following equations, it is possible to extract the reflected wave from the reflection point, that is, it is possible to perform reception focusing.

$$RF(i, T0)=\Sigma\Sigma ELE(i+k, j, T)$$

$$T=FD/V+Tr$$

Here, i+k indicates a scanning line, j indicates an element, one of two Σ indicates integration on k, and the other Σ indicates integration on j.

That is, when performing reception focusing in consideration of the fact that the reflected wave from the needle becomes an acoustic wave equivalent to a case in which a sound source is present at the symmetrical position with the needle as a specular reflection surface, the second reception focusing section 40B performs reception focusing so as to satisfy the following equations.

$$RF(i, T0)=\Sigma\Sigma ELE(i+k, j, T)$$

$$T=FD/V+Tr$$

$$Tr=\text{sqrt}(X^2+Y^2)/V$$

$$X=DX3+FD\times\sin(\phi+k\times EP)+R\times(\sin(k\times EP)-\sin((k+j)\times EP))$$

$$Y=DY3+FD\times\cos(\phi+k\times EP)+R\times(\cos(k\times EP)-\cos((k+j)\times EP))$$

$$DX3=2\times DX2$$

$$DY3=2\times DY2$$

$$DX2=2\times Rb\times\sin(k\times EP/2)\times\sin(\beta)\times\sin(\phi+\theta)+DX$$

$$DY2=2\times Rb\times\sin(k\times EP/2)\times\cos(\beta)\times\sin(\phi+\theta)+DY$$

$$DX=(V\times Tt-FD)\times\sin(\phi+\theta)$$

$$DY=(V\times Tt-FD)\times\cos(\phi+\theta)$$

Here, β=(k×EP/2)+φ+θ−arcsin(sin(φ)×FD/Rb)
Rb =sqrt(R²+FD²+2×R×FD ×cos(φ))

In this case, as in the case of using the linear type ultrasound probe, it is possible to improve the needle visualization performance. However, the visualization performance of the needle tip is reduced.

In addition, since the flow of the process performed by the main part of the ultrasound diagnostic device according to the fourth embodiment becomes the same process just by replacing the ultrasound probe in the third embodiment with a convex type ultrasound probe, the detailed explanation thereof will be omitted.

Setting φ=0 in the above equations when performing the reception focusing of the second reception focusing section 40B in the fourth embodiment corresponds to a case in which the transmission beam is not inclined. In addition, if integration on k is not performed, one of element reception signals that share the transmission focus is used.

In the case of the convex type ultrasound probe, the direction of the transmission beam differs depending on each scanning line. That is, the directions of the transmission beams spaced apart from each other by n elements are different by the angle n×EP. In consideration of the difference between the transmission beam directions of the scanning lines, θ of each RF(i, T0) may be shifted so as to always perform reception focusing in the same direction without depending on the scanning line in the above equations. That is, θ may be set as θ+n×EP, . . . , θ+EP, θ, θ−EP, . . . , θ−n×EP in reception focusing for generating RF(i−n, T0), . . . , RF(i−1, T0), RF(i, T0), RF(i+1, T0), . . . , RF(i+n, T0).

In each of the embodiments described above, the direction of the reception focus is set to θ. When sticking the needle in a state in which the needle is fixed to the needle guide or the like, θ determined by the fixture may be set in advance through the operating unit 32 or the like. When sticking the needle freehand, reception focusing may be performed in plural directions to generate needle images, and an image in which the needle is visualized best may be selected. As a method of determining an image in which a needle is visualized best, an image including the maximum brightness or an image having the maximum average brightness in the brightness distribution of a predetermined region in which it is assumed that a needle is included, an image that is linearly detected by the Hough transform or the like and has the maximum brightness in the straight line, or the like may be used.

In addition, an object to be visualized is not only the needle but also any reflector causing specular reflection. That is, in the reflector causing specular reflection, visualization may be reduced since sufficient specular reflection does not return to the reception opening depending on the transmission beam direction. However, as described above, using the fact that acoustic waves formed by transmission focusing propagate in various directions, it is possible to visualize the reflector satisfactorily without extra transmission.

In addition, each of the embodiments described above is also effective for the visualization of a reflector that does not cause specular reflection. That is, conventionally, even when there is no reflector below the probe and transmission steering (transmission with the inclined transmission beam) is required for visualization, visualization can be realized without performing extra transmission steering in various directions using the fact that acoustic waves formed by transmission focusing propagate not only to a region below the probe but also to the reflector. In this case, since the acoustic wave that spreads is used, the image quality is degraded compared with the transmission steering. However, it is possible to improve the image quality by using plural pieces of element data as in the second embodiment.

Although the case of generating an image of the needle has been described in each of the above embodiments, the present disclosure is effective not only for the generation of an image of the needle but also for the detection of the direction of the needle. That is, it can be determined that, after generating needle images by performing reception focusing in plural directions, the needle is stuck in a direction perpendicular to a direction in which an image having a needle visualized best is obtained. Alternatively, it is also possible to perform linear detection by the Hough transform or the like in an image having a needle visualized satisfactorily and to determine the direction of the straight line to be the direction of the needle.

In each of the embodiments described above, the generation of a B-mode image has been described. However, the present disclosure is effective for Doppler image generation as well as the B-mode image generation.

In addition, the processes performed by the respective units in each of the embodiments described above may be distributed as a program by being stored in various storage media.

In addition, the configuration, operation, and the like of the ultrasound diagnostic device described in each of the embodiments are examples, and it is needless to say that these can be changed according to the circumstances within the scope not deviating from the spirit of the present disclosure.

All documents, patent applications, and technical standards described in this specification are incorporated in this specification by reference to the same extent as when the incorporation of individual documents, patent applications, and technical standards by reference is described specifically and individually.

What is claimed is:

1. An ultrasound diagnostic device, comprising:
   a probe including a plurality of elements that generate and transmit ultrasound waves and receive ultrasound waves reflected from an inspection target;
   a transmission unit that transmits ultrasound waves from the plurality of elements so as to form a plurality of ultrasound beams that converge at a single transmission focus and diverge from the single transmission focus, wherein the single transmission focus is associated with a predetermined direction;
   a memory; and
   a processor coupled with the memory, wherein the processor is configured
      to perform first reception focusing for each reception signal received by each element of the probe according to reflection in a reception focusing direction that is different from the predetermined direction, the reception focusing direction being a direction that passes through the transmission focus and is inclined by an angle with respect to the predetermined direction, and
      to determine a direction of a needle based on a result of the first reception focusing.

2. The ultrasound diagnostic device according to claim 1, wherein the processor is further configured to:
   perform second reception focusing according to reflection in the predetermined direction.

3. The ultrasound diagnostic device according to claim 2, wherein the processor is further configured to:
   combine results of the first reception focusing and the second reception focusing.

4. The ultrasound diagnostic device according to claim 1, wherein the processor is further configured to perform the first reception focusing based on a delay time set.

5. The ultrasound diagnostic device according to claim 1, wherein the processor is further configured to perform the first reception focusing based on an assumption that there is specular reflection at each point in the reception focusing direction, and based on an assumption that there is a sound source at a second point that is different from each point in the reception focusing direction, and perform reception focusing for each point in the reception focusing direction based on a delay time for the assumed sound source.

6. The ultrasound diagnostic device according to claim 1, further comprising:
   an operating unit that is configured to receive a user designation of the reception focusing direction.

7. The ultrasound diagnostic device according to claim 6, wherein the operating unit is configured to receive the user designation of the reception focusing direction based on information related to a fixed direction of the needle.

8. The ultrasound diagnostic device according to claim 6, wherein the operating unit receives the user designation of the reception focusing direction based on a result of last first reception focusing performed by the processor.

9. An ultrasound diagnostic method, comprising:
   transmitting ultrasound waves from a plurality of elements of a probe so as to form a plurality of ultrasound beams that converge at a single transmission focus and diverge from the single transmission focus, the probe including the plurality of elements that generate and transmit ultrasound waves and receive ultrasound waves reflected from an inspection target; and wherein the single transmission focus is associated with a predetermined direction;
   performing first reception focusing for each reception signal received by each element of the probe according to reflection in a reception focusing direction that is different from the predetermined direction, the reception focusing direction being a direction that passes through the transmission focus and is inclined by an angle with respect to the predetermined direction, and
   determining a direction of a needle based on a result of the first reception focusing.

10. The ultrasound diagnostic method according to claim 9, further comprising:
    performing second reception focusing according to reflection in the predetermined direction.

11. The ultrasound diagnostic method according to claim 10, further comprising:
    combining results of the reception focusing of the first reception focusing and the second reception focusing.

12. The ultrasound diagnostic method according to claim 9, wherein the performing of the first reception focusing further includes performing reception focusing based on a delay time set.

13. The ultrasound diagnostic method according to claim 9, wherein the performing of the first reception focusing further includes performing the first reception focusing based on an assumption that there is specular reflection at each point in the reception focusing direction, and based on an assumption that there is a sound source at a second point that is different from each point in the reception focusing direction, and performing reception focusing for each point in the reception focusing direction based on a delay time for the assumed sound source.

14. The ultrasound diagnostic method according to claim 9, further comprising:
    designating the reception focusing direction.

15. The ultrasound diagnostic method according to claim 14, wherein the designating of the other direction further includes designating the reception focusing direction based on information related to a fixed direction of the needle.

16. The ultrasound diagnostic method according to claim 14, wherein the designating of the reception focusing direction further includes designating the reception focusing direction based on a result of the first second reception focusing that has been performed last time.

17. A non-transitory storage medium storing an ultrasound diagnostic program that causes a computer to execute processing comprising:
    controlling transmission of ultrasound waves from a plurality of elements of a probe so as to form a plurality of ultrasound beams that converge at a single transmission focus and diverge from the single transmission focus, the probe including the plurality of elements that generate and transmit ultrasound waves and receive ultrasound waves reflected from an inspection target; and wherein the single transmission focus is associated with a predetermined direction;

performing first reception focusing for each reception signal received by each element of the probe according to reflection in a reception focusing direction that is different from the predetermined direction, the reception focusing direction being a direction that passes through the transmission focus and is inclined by an angle with respect to the predetermined direction, and determining a direction of a needle based on a result of the first reception focusing.

18. The storage medium according to claim 17, wherein the processing further includes performing second reception focusing according to reflection in the predetermined direction.

19. The storage medium according to claim 18, wherein the processing further includes combining results of the reception focusing of the first reception focusing and the second reception focusing.

20. The storage medium according to claim 17, wherein the performing of the first reception focusing further includes performing reception focusing based on a delay time set.

21. The ultrasound diagnostic program according to claim 17, wherein the performing of the first reception focusing further includes performing the first reception focusing based on an assumption that there is assuming specular reflection at each point in the reception focusing direction, and based on an assumption that there is assuming a sound source at a different second point that is different from each point in the reception focusing direction, and performing reception focusing for each point in the reception focusing direction based on a delay time for the assumed sound source.

22. The ultrasound diagnostic program according to claim 17, wherein the processing further includes designating the reception focusing direction.

23. The ultrasound diagnostic program according to claim 22, wherein the designating of the other direction further includes designating the reception focusing direction based on information related to a fixed direction of the needle.

24. The ultrasound diagnostic program according to claim 22, wherein the designating of the reception focusing direction further includes designating the reception focusing direction based on a result of the first second reception focusing that has been performed last time.

* * * * *